(12) United States Patent
Tam

(10) Patent No.: US 7,732,138 B2
(45) Date of Patent: Jun. 8, 2010

(54) RAPID GENOTYPING ANALYSIS AND THE DEVICE THEREOF

(75) Inventor: Joseph Wing On Tam, Daly City, CA (US)

(73) Assignee: DiagCor Bioscience Incorporation Limited, Hong Kong (CN)

( * ) Notice: Subject to any disclaimer, the term of this patent is extended or adjusted under 35 U.S.C. 154(b) by 123 days.

(21) Appl. No.: 11/398,433

(22) Filed: Apr. 4, 2006

(65) Prior Publication Data

US 2006/0292601 A1    Dec. 28, 2006

Related U.S. Application Data

(63) Continuation-in-part of application No. 10/291,168, filed on Nov. 7, 2002, now abandoned, and a continuation-in-part of application No. 10/293,248, filed on Nov. 9, 2002.

(60) Provisional application No. 60/345,948, filed on Nov. 7, 2001.

(51) Int. Cl.
*C12Q 1/68* (2006.01)
*C12P 19/34* (2006.01)
*C07H 21/04* (2006.01)
*C12M 1/34* (2006.01)

(52) U.S. Cl. .................. 435/6; 435/91.1; 435/287.2; 536/23.1; 536/24.1

(58) Field of Classification Search .................. None
See application file for complete search history.

(56) References Cited

U.S. PATENT DOCUMENTS

| | | | |
|---|---|---|---|
| 5,310,650 A | 5/1994 | McMahon et al. | |
| 5,527,673 A | 6/1996 | Reinhartz et al. | |
| 5,550,039 A * | 8/1996 | Trachtenberg | 435/91.2 |
| 5,741,647 A | 4/1998 | Tam | |
| 6,020,187 A | 2/2000 | Tam | |
| 6,670,124 B1 * | 12/2003 | Chow et al. | 435/6 |
| 6,818,393 B1 | 11/2004 | Mach et al. | |
| 7,132,239 B2 | 11/2006 | Livak | |
| 2004/0185452 A1 | 9/2004 | Chen et al. | |
| 2008/0206773 A1 | 8/2008 | Tam | |

FOREIGN PATENT DOCUMENTS

| | | |
|---|---|---|
| CN | 1804043 A | 7/2006 |
| EP | 1746168 B1 | 4/2009 |
| WO | WO 03/100095 | 12/2003 |
| WO | WO 2004/023092 | 3/2004 |
| WO | WO 2007/115491 | 10/2007 |
| WO | PCT/CN2008/070671 | 4/2008 |
| WO | WO 2009/044370 | 4/2009 |

OTHER PUBLICATIONS

Buck et al (Biotechniques (1999) 27(3):528-536).*
HLA-DNA Tech, "Application Instruction for HLA DQB1 Genotyping Kit", printed 2008, pp. 1-5.*
Brightwell et al., Aug. 2002, "SNP genotyping using a simple and rapid single-tube modification of ARMS illustrated by analysis of 6 SNPs in a population of males with FRAXA repeat expansions", Molecular and Cellular Probes, vol. 16(4):297-305.
Chakraborty et al., Jul. 1996, "Paternity exclusion by DNA markers: effects of paternal mutations", Journal of Forensic Science, vol. 41(4): 671-677.
Edwards et al., Oct. 1991, "DNA typing and genetic mapping with trimeric and tetrameric landem repeats", American Journal of Human Genetics, vol. 49(4): 746-756.
Gill et al., Dec. 1985, "Forensic application of DNA 'fingerprints'", vol. 318(6046): 577-579.
Robinson et al., Jan. 2003, "IMGT/HLA and IMGT/MHC: sequence databases for the study of the major histocompatibility complex", Nucleic Acids Research, vol. 31(1):311-314.
Robinson et al., Jan. 2001, "IMGT/HLA Database—a sequence database for the human major histocompatibility complex", Nucleic Acids Research, vol. 29(1):210-213.
Thomas, E. Donnall, Sep. 1983, "Marrow Transplantation for Malignant Diseases", Journal of Clinical Oncology, vol. 1(9): 517-531.
Weiss, Kenneth M., Jul. 1998, "In search of human variation", Genome Research, vol. 8(7): 691-697.
Zhao et al., Jul. 1998, "Mapping of complex traits by single-nucleotide polymorphisms", American Journal of Human Genetics, vol. 63(1): 225-240.
Alonso et al., 2006, "Usefulness of Microchip Electrophoresis for the Analysis of Mitochonrial DNA in Forensic and Ancient DNA Studies", Electrophoresis, vol. 27(24): 5101-9.
Bouakaze et al., Nov. 2007, "First Successful Assay of Y-SNP Typing by SNaPshot minisequencing on Ancient DNA", International Journal of Legal Medicine, vol. 121(6): 493-499.
Budowle et al., Mar. 2005, "Forensic Aspects of Mass Disasters: Strategic Considerations for DNA-based Human Identification", Legal Medicine, vol. 7(1):230-243.
Divine, Anna-Maria, and Allen, Marie, 2005, "A DNA Microarray System for Forensic SNP analysis", Forensic Science International, vol. 154(1): 111-121.
Lee et al., Mar. 2005, "Selection of Twenty-Four Highly Informative SNP Markers for Human Identification and Paternity Analysis in Koreans", Forensic Science International, vol. 148(2-3): 107-112.

(Continued)

*Primary Examiner*—Sarae Bausch
(74) *Attorney, Agent, or Firm*—Law Offices of Albert Wai-Kit Chan, PLLC

(57) ABSTRACT

The present invention discloses the use of Allele-Specific-Oligonucleotide (ASO) as a detection assay for human HLA classification. Using Reversed-Dot-Blotting format and flow through hybridization process, more efficient, faster and less expensive HLA classification can be achieved. A simplified procedure for HLA genotyping is also described. This invention further provides a Single Nucleotide Polymorphism (SNP)-based DNA fingerprining method for rapid and accurate genotyping, identification as well as DNA analyses of genetic data from human beings and different organisms. In addition this invention also discloses a new device for rapid and sensitive analyses of nucleic acids, proteins and other analysts for diagnosis.

16 Claims, 21 Drawing Sheets

OTHER PUBLICATIONS

Onofori et al., May 2007, "Y-Chromosome Genetic Structure in Sub-Apennine Populations of Central Italy by SNP and STR Analysis", International Journal of Legal Medicine, vol. 121(3): 234-237.

Pakstis et al., May 2007, "Candidate SNPs for a Universal Individual Identification Panel", Human Genetics, vol. 121 (3-4): 305-317.

U.S. Appl. No. 10/291,168, filed Nov. 7, 2002, Tam, Joseph Wing On.

U.S. Appl. No. 10/293,248, filed Nov. 9, 2002, Tam, Joseph Wing On.

U.S. Appl. No. 12/044,126, filed Mar. 7, 2008, Tam, Joseph Wing On.

U.S. Appl. No. 60/345,948, filed Nov. 7, 2001, Tam, Joseph Wing On.

U.S. Appl. No. 60/910,208, filed Apr. 4, 2007, Tam, Joseph Wing On.

Bunce, M. et al., 1995, "Phototyping: Comprehensive DNA Typing for HLA-A,B,C, DRB1, DRB3, DRB4, DRB5, & DQB1 by PCR with 144 Primer Mixes Utilizing Sequence-Specific Primers", Tissue Antigens, vol. 46:355-367.

Dixon et al., 2005, "Validation of a 21-locus Autosomal SNP Multiplex for Forensic Identification Purposes", Forensic Science International vol. 154:62-72.

Huang et al., 2002, "Mutation patterns at Dinucleotide microsatellite loci in humans", American Journal of Human Genetics, vol. 70: 625-634.

Inagaki, S. et. al., 2004, "A new 39-plex analysis method for SNPs including 15 blood group loci", Forensic Science International vol. 144:45-57.

Kaneshige, T. et al., Feb. 1993, "Rapid and Practical HLA Class II Genotyping by Reversed Dot Blotting", Transplantation Proceedings, vol. 25(1): 194-198.

Kidd et al., 2006, "Developing a SNP panel for forensic identification of individuals", Forensic Science International, vol. 164: 20-32.

Lessig et al., 2005, "Y-SNP-genotyping—a new approach in forensic analysis", Forensic Science International, vol. 154: 128-136.

Li et al., 2006, "SNP genotyping by multplex amplification and microarrays assay for forensic application", Forensic Science International, vol. 162: 74-79.

Mach, B. et al., 1990, "Diversity and Regulation of MHC Class II Genes", In Molecular Biology of HLA Class II Antigens. ed. Silver J (CRC, Boca Raton, FL), pp. 201-223.

Michou et al., Apr. 28, 2006, "Validation of the Reshaped Shared Epitope HLA-DRB1 Classification in Rheumatoid Arthritis", Arthritis Research and Therapy, vol. 8(3): 1-6.

Reich et al., 2002, "Human genome sequence variation and the influence of gene history, mutation and recombination", Nature Genetics, vol. 32: 135-140.

Sanchez et al., 2006, "A multiplex assay with 52 single nucleotide polymorphisms for human identification", Electrophoresis vol. 27: 1713-1724.

Danyl Biotech, Aug. 11, 2003, "510(k) Summary", Submitted in accordance with the requirements of SMDA 1990 and 21 CFR 807.92.

Genovision, Oct. 27, 2006, "OLERUP SSP™ HLA Products From GenoVision: Full Product Review".

HLA-DNA-TECH, "Application Instruction for HLA DQB1 Genotyping Kit".

PCT International Search Report for International Application No. PCT/CN2007/001108, filed Apr. 4, 2007, Dated Aug. 16. 2007.

PCT Written Opinion of the International Searching Authority for International Application No. PCT/CN2007/001108, filed Apr. 4, 2007, Dated Aug. 16, 2007.

U.S. Office Action for Tam, Joseph Wing On, U.S. Appl. No. 10/291,168, filed Nov. 7, 2002, Dated Oct. 25, 2004.

U.S. Office Action for Tam, Joseph Wing On, U.S. Appl. No, 10/291,168, filed Nov. 7, 2002, Dated Mar. 21, 2005.

U.S. Office Action for Tam, Joseph Wing On, U.S. Appl. No. 10/291,168, filed Nov. 7, 2002, Dated Jan. 4, 2006.

U.S. Office Action for Tam, Joseph Wing On, U.S. Appl. No. 10/293,248, filed Nov. 9, 2002, Dated Sep. 7, 2007.

Allen et al., 2005, "Universal Tag Arrays in Forensic SNP Analysis", Methods in Molecular Biology, vol. 297:141-154.

Mitiaeva et al., Mar. 2007, "Development and Application of Hydrogel Oligonucleotide Microships for Forensic-Medical Personal Identification as Illustrated by ABO Locus", Sud. Med. Ekspert, vol. 50(2): 51-25.

Morling, N., Feb. 2003, "Forensic Genetics", Ugeskr Larger, vol. 165(9): 922-925.

Petkovski at al., May 2005, "SNPs and MALDI-TOF MS: Tools for DNA typing in Forensic Paternity Testing and Anthropology", Journal of Forensic Science, vol. 50(3): 535-541.

PCT International Search Report, Aug. 20, 2009, for PCT/IB2008/054044, filed Oct. 3, 2008.

U.S. Final Office Action, May 1, 2009, for U.S. Appl. No. 12/044,126, filed Mar. 7, 2008.

* cited by examiner

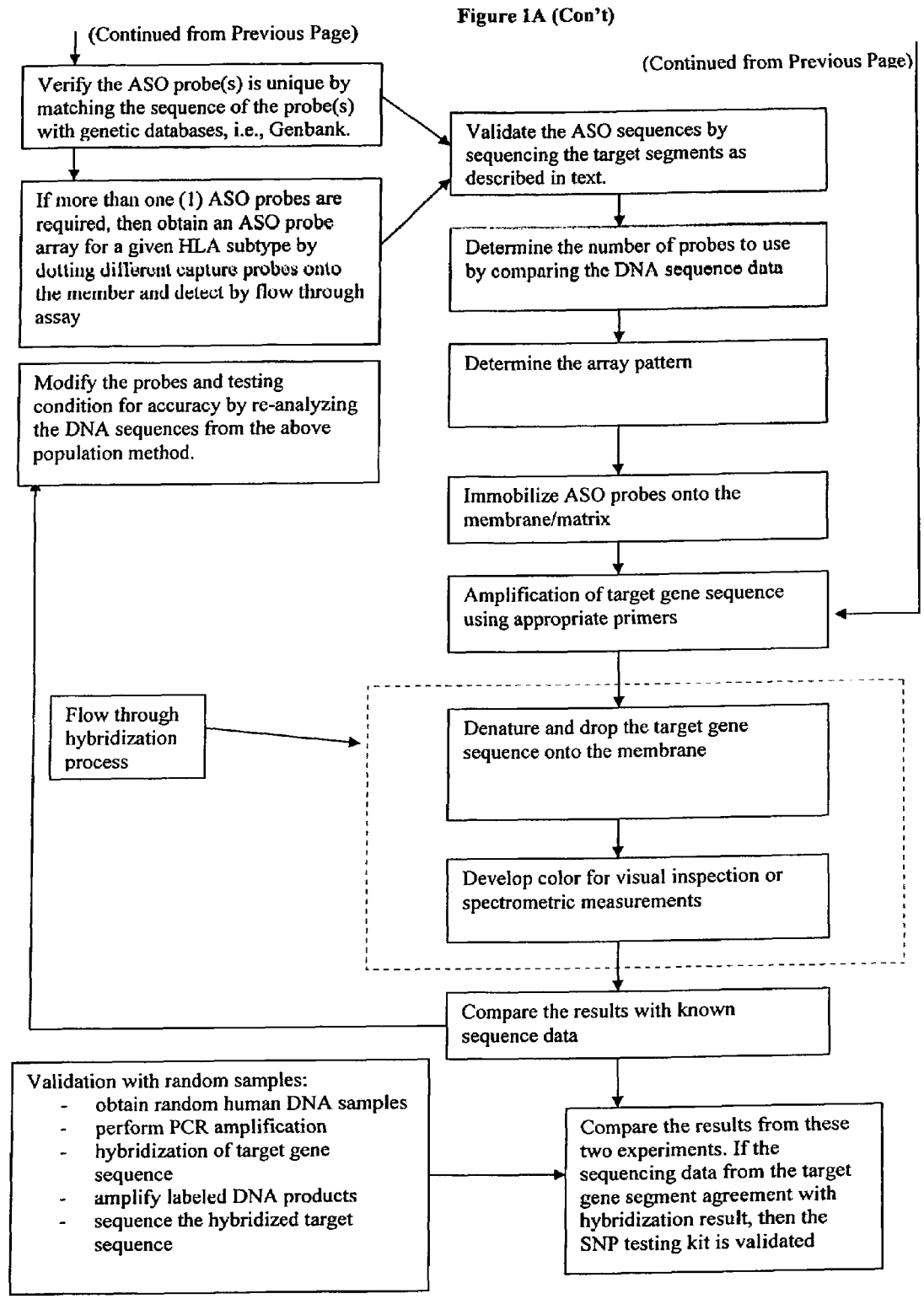
Figure 1A (Con't)

Figure 4

| Probe | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| 501 | + | | | | | | | | | | | | | | | | | |
| 502 | + | | | | | | | | + | | | | | | | | | |
| 5031 | + | | | | | | | | | | | | | | | | | |
| 5032 | + | | | | | | | | | | | | | | | | | |
| 504 | | + | | | | | | | + | | | | | | | | + | + |
| 6011 | | | | | | + | | | | | | | | | + | | | |
| 6012 | | | | | | + | | | | | | | | | + | + | | |
| 6013 | | | | | | + | | | | | | | | | + | | | |
| 602 | | | | + | | | | | | | | | | | | | | |
| 603 | | | | | + | | | | | | | | | | | | | |
| 604 | | | | | + | | | | | | | | | | | | | |
| 6051 | | | | | | + | | | | | | | | | | | | |
| 6052 | | | | | | + | | | | | | | | | | | | |
| 606 | | | | | | + | | | | | | | | | | | | |
| 607 | | | | | + | | | | | | | | | | | | | |
| 608 | | | | | + | | | | | | | | | | | | | |
| 609 | | | | | | + | | | | | | | | | | | | |
| 610 | | | + | | | | | | + | | | | | | | | | |
| 611 | | | + | | | | | | | | | | | | | | | |
| 612 | | | | | | | | | | | | | | | | | | |
| 613 | | | + | | + | | | | | | | | | | | | | |
| 614 | | | | + | | | | | | | | | | | | | | |
| 201 | | | | | | | | | | + | + | | | | | | + | |
| 202 | | | | | | | | | | + | + | | | | | | + | |
| 203 | | | | | | | | | | | + | + | | | | | + | |
| 3011 | | | | | | + | | | | | | | | + | | | | |
| 3012 | | | | | | + | | | | | | | | + | | | | |
| 302 | | | + | | | | | | | | | | | | | | | |
| 3032 | | | + | | | | | | | | | | | | | | | |
| 304 | | | | | | + | | | | | | | | + | | | | |
| 305 | | + | | | | | | + | | | | | | | | | | |
| 306 | | | + | | | | | | | | | | | | | | | |
| 307 | | | + | | | | | | | | | | | | | | | |
| 401 | | + | | | | | + | + | | | | | | + | | | | |
| 402 | | + | | | | | | + | | | | | | + | | | | |

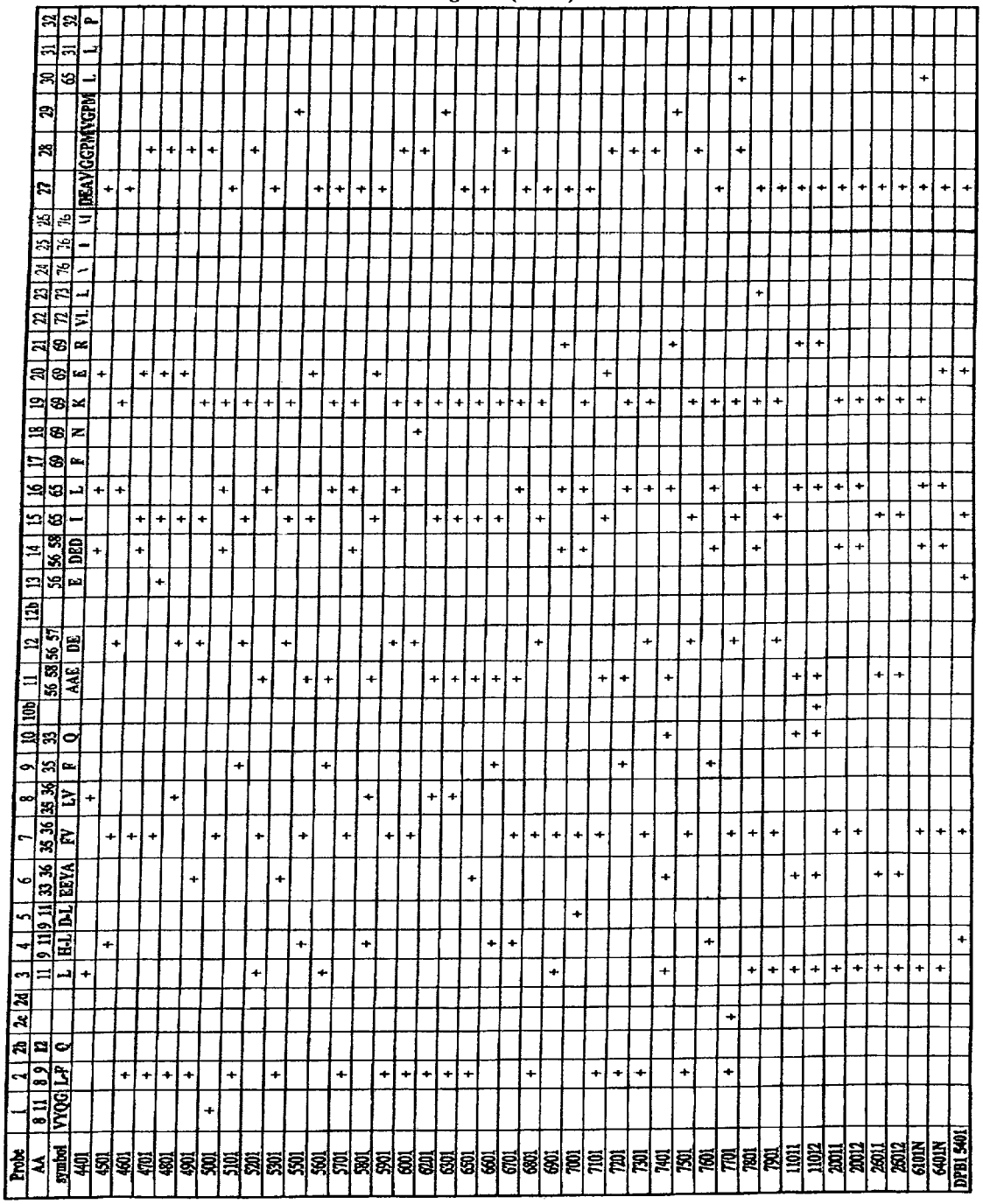
Figure 5 (Con't)

B. Typical images of *TWO* of the 20 Arrays testing for multiple genes or sequences.

A. a 20 Arrays membrane

A. Miniature DNA Lateral Flow Device

B. The Arrangement Structure for Multiple Miniature Devices

| Probe | 1 | 2 | 3 | 4 | 5 | 6 | 7 | 8 | 9 | 10 | 11 | 12 | 13 |
|---|---|---|---|---|---|---|---|---|---|---|---|---|---|
| Gene used | P53 codon 47 | P53 codon 72 | ApoE 112 | ApoE 158 | Col9A2 codon32 6 | Col9A2 codon32 6 | Col9A3 codon 25 | Col9A3 codon 435 | Col9A3 codon 70 | Beta-thal 26 (only one dot) | DPB#7 | DPB# 12 | DPB# 15 |

| 14 | 15 | 16 | 17 | 18 | 19 | 20 | 21 | 22 | 23 | 24 | 25 |
|---|---|---|---|---|---|---|---|---|---|---|---|
| DPB# 20 | DPB# 26 | DPB# 27 | DQB#3 | DQB#4 | DQB#5 | DQB#6 | BRCA694 | BRCA771 | BRCA871 | BRCQ10 38 | BRCQ11 83 |

Figure 11

HLA-DPB1 Gene typing results

| Samples | Genotype | | | Samples | Genotype | | |
|---|---|---|---|---|---|---|---|
| BR-101 | 0301/1301 | | | BR-134 | 6501/0501 | | |
| BR-102 | 0301/1301 | | | BR-135 | 0401/0401 | | |
| BR-104 | 4701/4801 | | | BR-136 | 0501/0501 | | |
| BR-105 | 0202/1701 | | | BR-139 | 2201/0402 | | |
| BR-109 | 0601/7901 | | | BR-140 | 0501/0501 | | |
| BR-110 | 02012/0501 | | | BR-141 | 0501/0501 | | |
| BR-111 | 0601/26012 | or | 2701/2901 | BR-142 | 0501/0301 | | |
| BR-112 | 0501/0301 | | | BR-145 | 1601/3901 | | |
| BR-113 | 0501/0401 | | | BR-146 | 02012/4801 | | |
| BR-116 | 0501/0202 | | | BR-147 | 0501/0501 | | |
| BR-117 | 0501/0501 | | | BR-148 | 0402/2201 | or | 0501/02012 |
| BR-118 | 02012/0202 | | | BR-149 | 0501/0202 | | |
| BR-119 | 0402/0501 | | | BR-150 | 0501/0501 | | |
| BR-120 | 0501/0501 | | | BR-137 | 2201/0402 | | |
| BR-121 | 0501/0501 | | | BR-138 | 0501/3101 | | |
| BR-122 | 0401/1701 | | | BR-143 | 0501/0402 | | |
| BR-123 | 02012/0202 | | | BR-144 | 1301/0402 | | |
| BR-124 | 0501/0501 | | | 31A | 0501/02012 | | |
| BR-125 | 02012/0101 | | | 31B | 02012/1301 | | |
| BR-126 | 0501/0401 | or | 2401/6301 | 32A | 02012/5001 | | |
| BR-127 | 0402/3301 | | | 32B | 0501/02012 | | |
| BR-128 | 1301/2101 | | | TH1A | 0501/1301 | | |
| BR-129 | 0501/0501 | | | TH1B | 0501/0501 | | |
| BR-130 | 0501/1901 | | | TH15A | 0501/0202 | | |
| BR-131 | 0501/02012 | | | TH15B | 0501/0401 | | |
| BR-132 | 0501/0501 | | | 20003 | 0501/0501 | | |
| BR-133 | 0501/02012 | | | TH2B | 0501/02012 | | |
| TH2A | 02012/5001 | | | | | | |

Table 1

Figure 12

Table 2 Allele and genotype frequencies of HLA-DPB1

| Genotype | n | Frequencies(n=47) (%) | Alleles | n | Frequencies(n=94) (%) |
|---|---|---|---|---|---|
| 0202/1701 | 1 | 2.13 | 101 | 1 | (1.06) |
| 0101/02012 | 1 | 2.13 | 2012 | 14 | (14.89) |
| 02012/0202 | 1 | 2.13 | 202 | 8 | (8.51) |
| 02012/1301 | 1 | 2.13 | 301 | 2 | (2.13) |
| 02012/4801 | 1 | 2.13 | 401 | 3 | (3.19) |
| 02012/5001 | 2 | 4.26 | 402 | 4 | (4.26) |
| 02012/6301 | 1 | 2.13 | 501 | 46 | (48.94) |
| 0301/1301 | 2 | 4.26 | 1301 | 6 | (6.38) |
| 0401/1701 | 1 | 2.13 | 1601 | 1 | (1.06) |
| 0402/3301 | 1 | 2.13 | 1701 | 2 | (2.13) |
| 0401/0401 | 1 | 2.13 | 1901 | 1 | (1.06) |
| 0501/02012 | 6 | 12.77 | 2101 | 1 | (1.06) |
| 0501/0202 | 3 | 6.38 | 3101 | 1 | (1.06) |
| 0501/0402 | 2 | 4.26 | 3301 | 1 | (1.06) |
| 0501/1301 | 1 | 2.13 | 3901 | 1 | (1.06) |
| 0501/1901 | 1 | 2.13 | 4101 | 1 | (1.06) |
| 0501/3101 | 1 | 2.13 | 4801 | 1 | (1.06) |
| 0501/4101 | 1 | 2.13 | 5001 | 2 | (2.13) |
| 0501/6501 | 1 | 2.13 | 6301 | 1 | (1.06) |
| 0501/0501 | 15 | 31.91 | 6501 | 1 | (1.06) |
| 1301/2101 | 1 | 2.13 | | | |
| 1301/0402 | 1 | 2.13 | | | |
| 1601/3901 | 1 | 2.13 | | | |

Table 2

Figure 13 (Tables 3 – 8)

Table 3. Oligonucleotide (ASO) Probe Sequences used for the identification of HLA-DRB specific alleles

| SEQ ID No. | Name | Codon | Sequence (5'→3') | Specificity (Allele) | Tm (°C) |
|---|---|---|---|---|---|
| 1 | (1) DRB1*01 | 26-32 | TTG CTG GAA AGA TGC AT | 1*01 all | 47.9 |
| 2 | (2) DRB1-03a | 69-73 | GAG CAG AAG CGG GG | 1*03 all, 1*0422, 1*1107, DRB3 all | 54 |
| 3 | DRB1*03b | 78-73 | CAG TAA TTG TCC ACC | 1*03012, 1*03022, 1*0104 | 46.26 |
| 4 | (3) DRB1*04b | 29-35 | AGATACTTCTATCACCAAGA | 1*0401, 1-0427 | 46.11 |
| 5 | (4) DRB1*07a | 78-74 | CAC GGT GTC CAC CTG | 1*0701, 1*0703 | 52 |
| 6 | DRB1-07b | 10-15 | CAG GGT AAG TAT AAG TGT | 1*07 all | 46.65 |
| 7 | (5) DRB1*08 | 74-69 | AGG GCC CGC CTG TC | 1*0801-08043, 1*0806-08017, 0819, 1*1604 1*0412,18,25, 1*1123, 1125 | 60 |
| 8 | (6) DRB1*09a | 8-13 | C TTG AAG CAG GAT AA | 1*09012 | 45 |
| 9 | DRB1*09b | 25-30 | TAT CTG CAC AGA GGC | 1*09012 | 44.7 |
| 10 | (7) DRB1*10a | 8-13 | TTG GAGGAGGTTAAGT | 1*1001 | 44.77 |
| 11 | DRB1*10b | 28-33 | A AGA CGC GTC CAT AA | 1*1001 | 47.94 |
| 12 | (8) DRB1*11 | 62-57 | TTC CAG TAC TCC TCA TCA | 1*11 all | 43.23 |
| 13 | (9) DRB1*12 | 35-40 | GAG CTC CTG CGC TTC | 1*1201-1204, 1*12021 1*12022, 1*1204 | 53.44 |
| 14 | (10) DRB1*13 | 73-69 | GGC CCG CTC GTC TT | 1*1301-1332 (1302,04,08,15*322) 1*1416, 1*0402, 1*0414 | 56.47 |
| 15 | (11) DRB1*14a | 62-56 | A GTG CTC CGC GCA | 1*1401-04,07,10,16,22, 25,26,28,31, 1*0707, 1*0310 | 53.42 |
| 16 | DRB1*14b | 74-70 | TCG GCC CGC CTC CT | 1*1407-11, 1*1414, 1*1418,23,26,28 | 62.68 |
| 17 | (12) DRB1*15 | 71-67 | CGC CTG CTC CAG GA | 1*15all, DRB5*0106 DRB5*0201-0204 | 55.85 |
| 18 | DRB1*15b | 10-15 | CAG CCT AAG AGG GAG T | 1*15all, 1*16all | 47.53 |
| 19 | (13) DRB1*1603 | 69-73 | AA GAC AGG GCC GCC | 1*1603 | 56.7 |
| 20 | (14) DRB1*1607 | 26-30 | CCC GGA CAG ATA CTT | 1*1607 | 45 |

Table 3. Oligonucleotide (ASO) Probe Sequences used for the identification of HLA-DRB specific alleles (con't)

| SEQ ID No. | Name | Codon | Sequence (5'→3') | Specificity (Allele) | Tm ( C ) |
|---|---|---|---|---|---|
| 21 | (15) DRB3a | 9-14 | GGAG CTG CTT AAG TCT ** * | DRB3*0103-0303 | 44.86 |
| 22 | DRB3b | 35-40 | GAG TTC CTG CGC TTC * * | DRB3*01, DRB1*1205 | 50 |
| 23 | DRB3c | 77-73 | ATT GTC CAC CTG GCC * ** * | DRB3*0202, *0204 DRB3*0206-0208 DRB3*0301-0302 | 52 |
| 24 | (16) DRB4a | 25-30 | TGG AAC CTG ATC AGA TAC * * * * *** | | 48.22 |
| 25 | DRB4b | 40-44 | GC TAC AAC AGT GACCTG | DRB4 all | 46.82 |
| 26 | (17) DRB5a | 26-30 | TTC CTG CAC AGA GAC * * * * * | DRB5*01011, 01012, 0104, -0107, 0109, 0201 | 44.07 |
| 27 | DRB5b | 26-30 | TTC CTG CAC AGA GGC * * * * * | DRB5*0102, 0103, 0108N DRB5*0201, 02012, 0203, 0204 | 51.43 |
| 28 | DRB5c | 35-40 | AGG AGG ACT TGC GCT T * * * | DRB5*0101, 01012, 0104, DRB5*0106, 0107, 0109 | 56.40 |
| 29 | (18) DRB all | 61-65 | TGG AAC AGC CAG AAG | DRB all | |

Table 4. PCR primers pairs for amplifying the HLA-DRB fragments

| SEQ ID No. | Name | Codon | Sequence (5'→3') | Tm (°C) |
|---|---|---|---|---|
| 97 | DRB-F1 | In intern-1 | ATCCTTCGTGTCCCCACAGCACG | |
| 98 | DRB-R1 | | GCCGCTGCACTGTGAAGCTCTC | |

Table 5. Oligonucleotide (ASO) Probe Sequences used for the identification of HLA-DQB1 specific alleles

| SEQ ID No. | Name | Codon | Sequence (5'→3') | Specificity | Tm(°C) |
|---|---|---|---|---|---|
| 30 | Probe1 | 26-31 | GT GTG ACC AGA CAC AT | 0501,0502,05031,05032, | 43 |
| 31 | Probe2 | 27-32 | GTGACCAGATACATCTATAA | 0504,0305,0401,0402, | 44.48 |
| 32 | Prboe3 | 24-30 | CGTCTTGTGACCAGATA | 0602,0610,0611,0613, 0302,0303,0306,0307, | 47.28 |
| 33 | Probe4 | 26-31 | CGTCTTGTAACCAGAC | 0603,0604,0607,0608,0614, | 43.28 |
| 34 | Probe5 | 25-31 | GTCTTGTAACCAGATACAT | 06051,06052,0606,0609, 0612, | 43.98 |
| 35 | Probe6 | 23-29 | CGTGCGTTATGTGA | 06011,06012,06013, 03011,03012,0304, | 44.33 |
| 36 | Probe7 | 20-26 | GGACCGAGCTCGTG | 0401, | 5 |
| 37 | Probe8 | 19-23 | ACCAACGGGACCGAG | 0305,0402,0401 | 55.99 |
| 38 | Probe8b | 19-24 | AACGGGACCGAGCG | 0305,0402, | 57.47 |
| 39 | Probe9 | 55-59 | GCCTAGCGCCGAGTA | 0502,0504,0610, | 54 |
| 40 | Probe10 |  | TGGGGCTGCCTGCC | 0201,0202 |  |
| 41 | Probe11 | 44-48 | GTGGGGGAGTTCCG | 0201,0202,0203, | 53.2 |
| 42 | Probe12 | 20-24 | TGCCTGACGCCGAG | 0203, | 57.12 |
| 43 | Probe13 | 20-25 | GCTTGACGCCGAGTA | 0401,0402, | 51.88 |
| 44 | Probe14 | 43-49 | CGACGTGGAGGTGTAC | 03011,03012,0304 | 50.55 |
| 45 | Probe15 | 34-39 | AGGAGGACGTGCGCT | 06013,06012,06011 | 56.06 |
| 46 | Probe16 |  | TATCGGGCGGTGACC | 06012, | 57.15 |
| 47 | Probe17 |  | GTGAGCAGAAGCATC | 0201,0202,0203 | 43.84 |
| 48 | Probe18 | 33-39 | CCGAGAAGAGTACGTGC | 0504, | 52.34 |
| 49 | Probe19 | 75-80 | GTGGACAGAGTGTGCA | 0502,05031 | 48.66 |
| 50 | Probe20 | 55-59 | CGCCTGCCGCCGAG | 0302,0304,0305,0307 | 65.33 |
| 51 | Probe21 | 55-59 | CGCCTGACGCCGAG | 03011,03012,03021, | 59.76 |
| 52 | Probe22 | 46-51 | TACCGGGCAGTGAC | 0501 | 48.63 |
| 53 | Probe23 | 55-60 | CTGTCGCCGACTAC | 06052; | 44.95 |

Table 6. PCR primers pairs for amplifying the HLA-DQB gene fragment

| SEQ ID No | Name | Codon | Sequence (5'-3') | Specificity | Tm(°C) |
|---|---|---|---|---|---|
| 99 | DQB-E2-F2 | -6 to 6 | CGGTGATTCCCCGCAGAGGAT | | |
| 100 | DQB-E2-R2 | 86-79 | CCACCTCGTAGTTGTGTCTGC | | |

Table 7. Oligonucleotide (ASO) Probe Sequences used for the identification of HLA-DPB specific alleles

| SEQ ID No. | Name | Position of amino acid | Sequence (5'→3') | Specificity (Allele) | Tm(°C) |
|---|---|---|---|---|---|
| 54 | SSO1 | 8-11 VYQG | AC GTG TAC CAG GGA C | 01011,01012,1501,1801,5001 | 46.07 |
| 55 | SSO2 | 8-9 LF | AC CTT TTC CAG GGA C | | 47.61 |
| 56 | SSO2b | 12 Q | G GGA CGA CAG GAA T | 02011 | 45.81 |
| 57 | SSO3 | 11 L | G TAC CAG TTA CGG CAG | 6401N | 47.03 |
| 58 | SSO4 | 8-11 H-L | GTG CAC CAG TTA CGG | | 48.5 |
| 59 | SSO5 | 8-11 D-L | T TAC GTG GAC CAG TTA | 7001, | 44.72 |
| 60 | SSO6 | 33-36 EEYA | GAG TAC GCG CGC TT | | 52.11 |
| 61 | SSO7 | 35-36 -FV | GAG TTC GTG CGC TT | | 48.32 |
| 62 | SSO8 | 35-36 -LV | GAG CTC GTG CGC TT | | 51.91 |
| 63 | SSO9 | 35 F | GAG TTC GCG CGC TT | 11011 | 55.18 |
| 64 | SSO10 | 33 Q | TAC AAC CGG CAG GAG | 1501, 7401, | 51.46 |
| 65 | SSO10b | 32 R | TAC AAC AGG CAG GAG | 11011 | 44.72 |
| 66 | SSO11 | 55-57 AAE | T GCT GCG GAG TAC T | | 45.23 |
| 67 | SSO12 | 55-56 DE | G CCT GAT GAG GAG TAC T | | 47.25 |
| 68 | SSO12b | 55-56 DE | CCT GAC GAG GAG TAC T | | 44.83 |
| 69 | SSO13 | 55 E | CT GAG GCG GAG TAC T | | 46.02 |
| 70 | SSO14 | 55-57 DED | G CCT GAT GAG GAC TAC T | | 47.25 |
| 71 | SSO15 | 65 I | G AAG GAC ATC CTG GA | | 46.08 |
| 72 | SSO16 | 65 L | AAG GAC CTC CTG GA | | 45.39 |
| 73 | SSO17 | 65 F | AG AAG GAC TTC CTG G | 4101 | 44.51 |
| 74 | SSO18 | 65 N | AG AAG GAC AAC CTG G | 6001 | 45.41 |
| 75 | SSO19 | 69 K | GAG AAG CGG GCA GT | | 50.22 |
| 76 | SSO20 | 69 E | GAG GAG CGG GCA GT | | 53.28 |
| 77 | SSO21 | 69 R | GAG AGG CGG GCA GT | 11011,11012, 1501,6901,7401, | 53.28 |
| 78 | SSO22 | 72 L | GCA TTG CCG GAC AG | 3101,3401 | 52.92 |
| 79 | SSO23 | 73 L | GCAGTG CTG GAC AGG | 7801, | 51.83 |
| 80 | SSO24 | 76 V | C AGG GTA TGC AGA CA | | 45.43 |

Table 7. Oligonucleotide (ASO) Probe Sequences used for the identification of HLA-DPB specific alleles (con't)

| SEQ ID No. | Name | Position of amino acid | Sequence (5'→3') | Specificity (Allele) | Tm(°C) |
|---|---|---|---|---|---|
| 81 | SSO25 | 76 I | AC AGG ATA TGC AGA CA * | | 43.95 |
| 82 | SSO26 | 76 M | AC AGG ATG TGC AGA C * * | | 43.47 |
| 83 | SSO27 | 83-86 DEAV | TAC GAG CTG GAC GAG | | 48.43 |
| 84 | SSO28 | 83-86 GGPM | TAC GAG CTG GGC GG * | | 55.89 |
| 85 | SSO29 | 83-86 VGPM | TAC GAG CTG GTC GG * | | 49.2 |
| 86 | SSO30 | 61-66 | AA GGA CCT CCT GTA GG * * | 6101N | 47.05 |
| 87 | SSO31 | 10-14 | CA GGG ACT GCA GGA A * | 7701 | 46.9 |
| 88 | SSO32 | 14-19 | AATG CTACCC GTTTA | 3801 | 44.11 |
| 89 | | 6-12 | TAAGTGTACCAGTTACGG ** | 6401N | 46.33 |
| 90 | | 30-34 | ATCTACAACCGGCAG * * | 1501, 7401 | |
| 91 | | 40-46 | GACGTGGGAGAGTTC * | 01012, 11011, 11012, 1501, 26011 | 45.57 |
| 92 | | 61-66 | AAGGACCTCCTGTAGG * * | 6101N | 47.05 |
| 93 | | 69-74 | AAGCGGGCATTGCC * | 3101, 3401 | 57.5 |
| 94 | | 70-74 | GGGCAGTGCTAGAC * | 7801 | 43.63 |
| 95 | | 14-19 | AATGCTACCCGTTTA * | 3801 | 44.11 |
| 96 | | 7-12 | TTACGTGGACCAGT * | 7001 | 45.14 |

Table 8. Primers for HLA-DPB gene fragment (f: forwards and r: backwards primers)

| SEQ ID No | Name | Position of amino acid | Sequence (5'→3') | Tm(°C) |
|---|---|---|---|---|
| 101 | Primer1-f | 3-9 | GCCACTCCAGAGAATTACCTTTT | 60.02 |
| 102 | Primer2-f | 4-9 | CCAGAGAATTACGTGTACCAGTT | 57.39 |
| 103 | Primer3-f | 4-11 | CCAGAGAATTACGTGCACCAGTT | 62.62 |
| 104 | Primer4-r | 89-84 | CAGGGTCATGGGCCCGC | 68 |
| 105 | Primer5-f | 90-84 | GCAGGGTCATGGGCCCGA | 70 |
| 106 | Primer6-r | 89-84 | CAGCGTCACGGCCTCGTC | 65.34 |

SEQUENCE LISTING

<160> NUMBER OF SEQ ID NOS: 106

<210> SEQ ID NO 1
<211> LENGTH: 17
<212> TYPE: DNA
<213> ORGANISM: Homo sapiens

<400> SEQUENCE: 1
ttgctggaaa gatgcat                                              17

<210> SEQ ID NO 2
<211> LENGTH: 14
<212> TYPE: DNA
<213> ORGANISM: Homo sapiens

<400> SEQUENCE: 2
gagcagaagc gggg                                                 14

<210> SEQ ID NO 3
<211> LENGTH: 15
<212> TYPE: DNA
<213> ORGANISM: Homo sapiens

<400> SEQUENCE: 3

```
cagtaattg tccacc                                                    15

<210> SEQ ID NO 4
<211> LENGTH: 20
<212> TYPE: DNA
<213> ORGANISM: Homo sapiens

<400> SEQUENCE: 4
agatacttct atcaccaaga                                               20

<210> SEQ ID NO 5
<211> LENGTH: 15
<212> TYPE: DNA
<213> ORGANISM: Homo sapiens

<400> SEQUENCE: 5
cacggtgtcc acctg                                                    15

<210> SEQ ID NO 6
<211> LENGTH: 18
<212> TYPE: DNA
<213> ORGANISM: Homo sapiens

<400> SEQUENCE: 6
cagggtaagt ataagtgt                                                 18

<210> SEQ ID NO 7
<211> LENGTH: 14
<212> TYPE: DNA
<213> ORGANISM: Homo sapiens

<400> SEQUENCE: 7
agggcccgcc tgtc                                                     14

<210> SEQ ID NO 8
<211> LENGTH: 15
<212> TYPE: DNA
<213> ORGANISM: Homo sapiens

<400> SEQUENCE: 8
cttgaagcag gataa                                                    15

<210> SEQ ID NO 9
<211> LENGTH: 15
<212> TYPE: DNA
<213> ORGANISM: Homo sapiens

<400> SEQUENCE: 9
tatctgcaca gaggc                                                    15

<210> SEQ ID NO 10
<211> LENGTH: 16
<212> TYPE: DNA
<213> ORGANISM: Homo sapiens

<400> SEQUENCE: 10
ttggaggagg ttaagt                                                   16

<210> SEQ ID NO 11
<211> LENGTH: 15
<212> TYPE: DNA
<213> ORGANISM: Homo sapiens
```

```
<400> SEQUENCE: 11
aagacgcgtc cataa                                                      15

<210> SEQ ID NO 12
<211> LENGTH: 18
<212> TYPE: DNA
<213> ORGANISM: Homo sapiens

<400> SEQUENCE: 12
ttccagtact cctcatca                                                   18

<210> SEQ ID NO 13
<211> LENGTH: 15
<212> TYPE: DNA
<213> ORGANISM: Homo sapiens

<400> SEQUENCE: 13
gagctcctgc gcttc                                                      15

<210> SEQ ID NO 14
<211> LENGTH: 14
<212> TYPE: DNA
<213> ORGANISM: Homo sapiens

<400> SEQUENCE: 14
ggcccgctcg tctt                                                       14

<210> SEQ ID NO 15
<211> LENGTH: 13
<212> TYPE: DNA
<213> ORGANISM: Homo sapiens

<400> SEQUENCE: 15
agtgctccgc gca                                                        13

<210> SEQ ID NO 16
<211> LENGTH: 14
<212> TYPE: DNA
<213> ORGANISM: Homo sapiens

<400> SEQUENCE: 16
tcggcccgcc tcct                                                       14

<210> SEQ ID NO 17
<211> LENGTH: 14
<212> TYPE: DNA
<213> ORGANISM: Homo sapiens

<400> SEQUENCE: 17
cgcctgctcc agga                                                       14

<210> SEQ ID NO 18
<211> LENGTH: 16
<212> TYPE: DNA
<213> ORGANISM: Homo sapiens

<400> SEQUENCE: 18
cagcctaaga gggagt                                                     16

<210> SEQ ID NO 19
<211> LENGTH: 14
<212> TYPE: DNA
<213> ORGANISM: Homo sapiens
```

<400> SEQUENCE: 19
aagacagggc cgcc                                                          14

<210> SEQ ID NO 20
<211> LENGTH: 15
<212> TYPE: DNA
<213> ORGANISM: Homo sapiens

<400> SEQUENCE: 20
cccggacaga tactt                                                         15

<210> SEQ ID NO 21
<211> LENGTH: 16
<212> TYPE: DNA
<213> ORGANISM: Homo sapiens

<400> SEQUENCE: 21
ggagctgctt aagtct                                                        16

<210> SEQ ID NO 22
<211> LENGTH: 15
<212> TYPE: DNA
<213> ORGANISM: Homo sapiens

<400> SEQUENCE: 22
gagttcctgc gcttc                                                         15

<210> SEQ ID NO 23
<211> LENGTH: 15
<212> TYPE: DNA
<213> ORGANISM: Homo sapiens

<400> SEQUENCE: 23
attgtccacc tggcc                                                         15

<210> SEQ ID NO 24
<211> LENGTH: 18
<212> TYPE: DNA
<213> ORGANISM: Homo sapiens

<400> SEQUENCE: 24
tggaacctga tcagatac                                                      18

<210> SEQ ID NO 25
<211> LENGTH: 17
<212> TYPE: DNA
<213> ORGANISM: Homo sapiens

<400> SEQUENCE: 25
gctacaacag tgacctg                                                       17

<210> SEQ ID NO 26
<211> LENGTH: 15
<212> TYPE: DNA
<213> ORGANISM: Homo sapiens

<400> SEQUENCE: 26
ttcctgcaca gagac                                                         15

<210> SEQ ID NO 27
<211> LENGTH: 15
<212> TYPE: DNA

<213> ORGANISM: Homo sapiens

<400> SEQUENCE: 27
ttcctgcaca gaggc                                                        15

<210> SEQ ID NO 28
<211> LENGTH: 16
<212> TYPE: DNA
<213> ORGANISM: Homo sapiens

<400> SEQUENCE: 28
aggaggactt gcgctt                                                       16

<210> SEQ ID NO 29
<211> LENGTH: 15
<212> TYPE: DNA
<213> ORGANISM: Homo sapiens

<400> SEQUENCE: 29
tggaacagcc agaag                                                        15

<210> SEQ ID NO 30
<211> LENGTH: 16
<212> TYPE: DNA
<213> ORGANISM: Homo sapiens

<400> SEQUENCE: 30
gtgtgaccag acacat                                                       16

<210> SEQ ID NO 31
<211> LENGTH: 20
<212> TYPE: DNA
<213> ORGANISM: Homo sapiens

<400> SEQUENCE: 31
gtgaccagat acatctataa                                                   20

<210> SEQ ID NO 32
<211> LENGTH: 17
<212> TYPE: DNA
<213> ORGANISM: Homo sapiens

<400> SEQUENCE: 32
cgtcttgtga ccagata                                                      17

<210> SEQ ID NO 33
<211> LENGTH: 16
<212> TYPE: DNA
<213> ORGANISM: Homo sapiens

<400> SEQUENCE: 33
cgtcttgtaa ccagac                                                       16

<210> SEQ ID NO 34
<211> LENGTH: 19
<212> TYPE: DNA
<213> ORGANISM: Homo sapiens

<400> SEQUENCE: 34
gtcttgtaac cagatacat                                                    19

<210> SEQ ID NO 35
<211> LENGTH: 14

```
<212> TYPE: DNA
<213> ORGANISM: Homo sapiens

<400> SEQUENCE: 35
cgtgcgttat gtga                                                       14

<210> SEQ ID NO 36
<211> LENGTH: 14
<212> TYPE: DNA
<213> ORGANISM: Homo sapiens

<400> SEQUENCE: 36
ggaccgagct cgtg                                                       14

<210> SEQ ID NO 37
<211> LENGTH: 15
<212> TYPE: DNA
<213> ORGANISM: Homo sapiens

<400> SEQUENCE: 37
accaacggga ccgag                                                      15

<210> SEQ ID NO 38
<211> LENGTH: 14
<212> TYPE: DNA
<213> ORGANISM: Homo sapiens

<400> SEQUENCE: 38
aacgggaccg agcg                                                       14

<210> SEQ ID NO 39
<211> LENGTH: 15
<212> TYPE: DNA
<213> ORGANISM: Homo sapiens

<400> SEQUENCE: 39
gcctagcgcc gagta                                                      15

<210> SEQ ID NO 40
<211> LENGTH: 14
<212> TYPE: DNA
<213> ORGANISM: Homo sapiens

<400> SEQUENCE: 40
tggggctgcc tgcc                                                       14

<210> SEQ ID NO 41
<211> LENGTH: 14
<212> TYPE: DNA
<213> ORGANISM: Homo sapiens

<400> SEQUENCE: 41
gtgggggagt tccg                                                       14

<210> SEQ ID NO 42
<211> LENGTH: 14
<212> TYPE: DNA
<213> ORGANISM: Homo sapiens

<400> SEQUENCE: 42
tgcctgacgc cgag                                                       14

<210> SEQ ID NO 43
```

-continued

```
<211> LENGTH: 15
<212> TYPE: DNA
<213> ORGANISM: Homo sapiens

<400> SEQUENCE: 43
gcttgacgcc gagta                                                          15

<210> SEQ ID NO 44
<211> LENGTH: 16
<212> TYPE: DNA
<213> ORGANISM: Homo sapiens

<400> SEQUENCE: 44
cgacgtggag gtgtac                                                         16

<210> SEQ ID NO 45
<211> LENGTH: 15
<212> TYPE: DNA
<213> ORGANISM: Homo sapiens

<400> SEQUENCE: 45
aggaggacgt gcgct                                                          15

<210> SEQ ID NO 46
<211> LENGTH: 15
<212> TYPE: DNA
<213> ORGANISM: Homo sapiens

<400> SEQUENCE: 46
tatcgggcgg tgacc                                                          15

<210> SEQ ID NO 47
<211> LENGTH: 15
<212> TYPE: DNA
<213> ORGANISM: Homo sapiens

<400> SEQUENCE: 47
gtgagcagaa gcatc                                                          15

<210> SEQ ID NO 48
<211> LENGTH: 17
<212> TYPE: DNA
<213> ORGANISM: Homo sapiens

<400> SEQUENCE: 48
ccgagaagag tacgtgc                                                        17

<210> SEQ ID NO 49
<211> LENGTH: 16
<212> TYPE: DNA
<213> ORGANISM: Homo sapiens

<400> SEQUENCE: 49
gtggacagag tgtgca                                                         16

<210> SEQ ID NO 50
<211> LENGTH: 14
<212> TYPE: DNA
<213> ORGANISM: Homo sapiens

<400> SEQUENCE: 50
cgcctgccgc cgag                                                           14
```

```
<210> SEQ ID NO 51
<211> LENGTH: 14
<212> TYPE: DNA
<213> ORGANISM: Homo sapiens

<400> SEQUENCE: 51
cgcctgacgc cgag                                                          14

<210> SEQ ID NO 52
<211> LENGTH: 14
<212> TYPE: DNA
<213> ORGANISM: Homo sapiens

<400> SEQUENCE: 52
taccgggcag tgac                                                          14

<210> SEQ ID NO 53
<211> LENGTH: 14
<212> TYPE: DNA
<213> ORGANISM: Homo sapiens

<400> SEQUENCE: 53
ctgtcgccga ctac                                                          14

<210> SEQ ID NO 54
<211> LENGTH: 15
<212> TYPE: DNA
<213> ORGANISM: Homo sapiens

<400> SEQUENCE: 54
acgtgtacca gggac                                                         15

<210> SEQ ID NO 55
<211> LENGTH: 15
<212> TYPE: DNA
<213> ORGANISM: Homo sapiens

<400> SEQUENCE: 55
accttttcca gggac                                                         15

<210> SEQ ID NO 56
<211> LENGTH: 14
<212> TYPE: DNA
<213> ORGANISM: Homo sapiens

<400> SEQUENCE: 56
gggacgacag gaat                                                          14

<210> SEQ ID NO 57
<211> LENGTH: 16
<212> TYPE: DNA
<213> ORGANISM: Homo sapiens

<400> SEQUENCE: 57
gtaccagtta cggcag                                                        16

<210> SEQ ID NO 58
<211> LENGTH: 15
<212> TYPE: DNA
<213> ORGANISM: Homo sapiens

<400> SEQUENCE: 58
gtgcaccagt tacgg                                                         15
```

```
<210> SEQ ID NO 59
<211> LENGTH: 16
<212> TYPE: DNA
<213> ORGANISM: Homo sapiens

<400> SEQUENCE: 59
ttacgtggac cagtta                                                    16

<210> SEQ ID NO 60
<211> LENGTH: 14
<212> TYPE: DNA
<213> ORGANISM: Homo sapiens

<400> SEQUENCE: 60
gagtacgcgc gctt                                                      14

<210> SEQ ID NO 61
<211> LENGTH: 14
<212> TYPE: DNA
<213> ORGANISM: Homo sapiens

<400> SEQUENCE: 61
gagttcgtgc gctt                                                      14

<210> SEQ ID NO 62
<211> LENGTH: 14
<212> TYPE: DNA
<213> ORGANISM: Homo sapiens

<400> SEQUENCE: 62
gagctcgtgc gctt                                                      14

<210> SEQ ID NO 63
<211> LENGTH: 14
<212> TYPE: DNA
<213> ORGANISM: Homo sapiens

<400> SEQUENCE: 63
gagttcgcgc gctt                                                      14

<210> SEQ ID NO 64
<211> LENGTH: 15
<212> TYPE: DNA
<213> ORGANISM: Homo sapiens

<400> SEQUENCE: 64
tacaaccggc aggag                                                     15

<210> SEQ ID NO 65
<211> LENGTH: 15
<212> TYPE: DNA
<213> ORGANISM: Homo sapiens

<400> SEQUENCE: 65
tacaacaggc aggag                                                     15

<210> SEQ ID NO 66
<211> LENGTH: 14
<212> TYPE: DNA
<213> ORGANISM: Homo sapiens

<400> SEQUENCE: 66
tgctgcggag tact                                                      14
```

```
<210> SEQ ID NO 67
<211> LENGTH: 16
<212> TYPE: DNA
<213> ORGANISM: Homo sapiens

<400> SEQUENCE: 67
gcctgatgag gagtac                                                   16

<210> SEQ ID NO 68
<211> LENGTH: 16
<212> TYPE: DNA
<213> ORGANISM: Homo sapiens

<400> SEQUENCE: 68
cctgacgagg agtact                                                   16

<210> SEQ ID NO 69
<211> LENGTH: 15
<212> TYPE: DNA
<213> ORGANISM: Homo sapiens

<400> SEQUENCE: 69
ctgaggcgga gtact                                                    15

<210> SEQ ID NO 70
<211> LENGTH: 17
<212> TYPE: DNA
<213> ORGANISM: Homo sapiens

<400> SEQUENCE: 70
gcctgatgag gactact                                                  17

<210> SEQ ID NO 71
<211> LENGTH: 15
<212> TYPE: DNA
<213> ORGANISM: Homo sapiens

<400> SEQUENCE: 71
gaaggacatc ctgga                                                    15

<210> SEQ ID NO 72
<211> LENGTH: 14
<212> TYPE: DNA
<213> ORGANISM: Homo sapiens

<400> SEQUENCE: 72
aaggacctcc tgga                                                     14

<210> SEQ ID NO 73
<211> LENGTH: 15
<212> TYPE: DNA
<213> ORGANISM: Homo sapiens

<400> SEQUENCE: 73
agaaggactt cctgg                                                    15

<210> SEQ ID NO 74
<211> LENGTH: 15
<212> TYPE: DNA
<213> ORGANISM: Homo sapiens

<400> SEQUENCE: 74
```

```
agaaggacaa cctgg                                                    15

<210> SEQ ID NO 75
<211> LENGTH: 14
<212> TYPE: DNA
<213> ORGANISM: Homo sapiens

<400> SEQUENCE: 75
gagaagcggg cagt                                                     14

<210> SEQ ID NO 76
<211> LENGTH: 14
<212> TYPE: DNA
<213> ORGANISM: Homo sapiens

<400> SEQUENCE: 76
gaggagcggg cagt                                                     14

<210> SEQ ID NO 77
<211> LENGTH: 14
<212> TYPE: DNA
<213> ORGANISM: Homo sapiens

<400> SEQUENCE: 77
gagaggcggg cagt                                                     14

<210> SEQ ID NO 78
<211> LENGTH: 14
<212> TYPE: DNA
<213> ORGANISM: Homo sapiens

<400> SEQUENCE: 78
gcattgccgg acag                                                     14

<210> SEQ ID NO 79
<211> LENGTH: 15
<212> TYPE: DNA
<213> ORGANISM: Homo sapiens

<400> SEQUENCE: 79
gcagtgctgg acagg                                                    15

<210> SEQ ID NO 80
<211> LENGTH: 15
<212> TYPE: DNA
<213> ORGANISM: Homo sapiens

<400> SEQUENCE: 80
cagggtatgc agaca                                                    15

<210> SEQ ID NO 81
<211> LENGTH: 16
<212> TYPE: DNA
<213> ORGANISM: Homo sapiens

<400> SEQUENCE: 81
acaggatatg cagaca                                                   16

<210> SEQ ID NO 82
<211> LENGTH: 15
<212> TYPE: DNA
<213> ORGANISM: Homo sapiens

<400> SEQUENCE: 82
```
acaggatgtg cagac                                          15

<210> SEQ ID NO 83
<211> LENGTH: 15
<212> TYPE: DNA
<213> ORGANISM: Homo sapiens

<400> SEQUENCE: 83
tacgagctgg acgag                                          15

<210> SEQ ID NO 84
<211> LENGTH: 14
<212> TYPE: DNA
<213> ORGANISM: Homo sapiens

<400> SEQUENCE: 84
tacgagctgg gcgg                                           14

<210> SEQ ID NO 85
<211> LENGTH: 14
<212> TYPE: DNA
<213> ORGANISM: Homo sapiens

<400> SEQUENCE: 85
tacgagctgg tcgg                                           14

<210> SEQ ID NO 86
<211> LENGTH: 16
<212> TYPE: DNA
<213> ORGANISM: Homo sapiens

<400> SEQUENCE: 86
aaggacctcc tgtagg                                         16

<210> SEQ ID NO 87
<211> LENGTH: 15
<212> TYPE: DNA
<213> ORGANISM: Homo sapiens

<400> SEQUENCE: 87
cagggactgc aggaa                                          15

<210> SEQ ID NO 88
<211> LENGTH: 15
<212> TYPE: DNA
<213> ORGANISM: Homo sapiens

<400> SEQUENCE: 88
aatgctaccc gttta                                          15

<210> SEQ ID NO 89
<211> LENGTH: 18
<212> TYPE: DNA
<213> ORGANISM: Homo sapiens

<400> SEQUENCE: 89
taagtgtacc agttacgg                                       18

<210> SEQ ID NO 90
<211> LENGTH: 15
<212> TYPE: DNA
<213> ORGANISM: Homo sapiens

```
<400> SEQUENCE: 90
atctacaacc ggcag                                                    15

<210> SEQ ID NO 91
<211> LENGTH: 15
<212> TYPE: DNA
<213> ORGANISM: Homo sapiens

<400> SEQUENCE: 91
gacgtgggag agttc                                                    15

<210> SEQ ID NO 92
<211> LENGTH: 16
<212> TYPE: DNA
<213> ORGANISM: Homo sapiens

<400> SEQUENCE: 92
aaggacctcc tgtagg                                                   16

<210> SEQ ID NO 93
<211> LENGTH: 14
<212> TYPE: DNA
<213> ORGANISM: Homo sapiens

<400> SEQUENCE: 93
aagcgggcat tgcc                                                     14

<210> SEQ ID NO 94
<211> LENGTH: 14
<212> TYPE: DNA
<213> ORGANISM: Homo sapiens

<400> SEQUENCE: 94
gggcagtgct agac                                                     14

<210> SEQ ID NO 95
<211> LENGTH: 15
<212> TYPE: DNA
<213> ORGANISM: Homo sapiens

<400> SEQUENCE: 95
aatgctaccc gttta                                                    15

<210> SEQ ID NO 96
<211> LENGTH: 14
<212> TYPE: DNA
<213> ORGANISM: Homo sapiens

<400> SEQUENCE: 96
ttacgtggac cagt                                                     14

<210> SEQ ID NO 97
<211> LENGTH: 23
<212> TYPE: DNA
<213> ORGANISM: Homo sapiens

<400> SEQUENCE: 97
atccttcgtg tccccacagc acg                                           23

<210> SEQ ID NO 98
<211> LENGTH: 22
<212> TYPE: DNA
<213> ORGANISM: Homo sapiens
```

<400> SEQUENCE: 98
gccgctgcac tgtgaagctc tc                                          22

<210> SEQ ID NO 99
<211> LENGTH: 21
<212> TYPE: DNA
<213> ORGANISM: Homo sapiens

<400> SEQUENCE: 99
cggtgattcc ccgcagagga t                                           21

<210> SEQ ID NO 100
<211> LENGTH: 21
<212> TYPE: DNA
<213> ORGANISM: Homo sapiens

<400> SEQUENCE: 100
ccacctcgta gttgtgtctg c                                           21

<210> SEQ ID NO 101
<211> LENGTH: 23
<212> TYPE: DNA
<213> ORGANISM: Homo sapiens

<400> SEQUENCE: 101
gccactccag agaattacct ttt                                         23

<210> SEQ ID NO 102
<211> LENGTH: 23
<212> TYPE: DNA
<213> ORGANISM: Homo sapiens

<400> SEQUENCE: 102
ccagagaatt acgtgtacca gtt                                         23

<210> SEQ ID NO 103
<211> LENGTH: 23
<212> TYPE: DNA
<213> ORGANISM: Homo sapiens

<400> SEQUENCE: 103
ccagagaatt acgtgcacca gtt                                         23

<210> SEQ ID NO 104
<211> LENGTH: 17
<212> TYPE: DNA
<213> ORGANISM: Homo sapiens

<400> SEQUENCE: 104
cagggtcatg ggcccgc                                                17

<210> SEQ ID NO 105
<211> LENGTH: 18
<212> TYPE: DNA
<213> ORGANISM: Homo sapiens

<400> SEQUENCE: 105
gcagggtcat gggcccga                                               18

<210> SEQ ID NO 106
<211> LENGTH: 18
<212> TYPE: DNA

```
<213> ORGANISM: Homo sapiens

<400> SEQUENCE: 106
cagggtcacg gcctcgtc                                                    18
```

RAPID GENOTYPING ANALYSIS AND THE DEVICE THEREOF

This application is a continuation-in-part of U.S. Ser. No. 10/291,168, filed Nov. 7, 2002, now abandoned which claims the benefit of U.S. Ser. No. 60/345,948, filed Nov. 7, 2001, and is a continuation-in-part of U.S. Ser. No. 10/293,248, and filed Nov. 9, 2002. The contents of these preceding applications are hereby incorporated in their entireties by reference into this application.

Throughout this application, various publications are referenced. Disclosures of these publications in their entireties are hereby incorporated in their entireties by reference into this application in order to more fully describe the state of the art to which this invention pertains.

BACKGROUND OF THE PRESENT INVENTION

1. Field of Invention

The present invention relates to a method of making rapid, definitive identification of human leukocytic antigens (HLA) by DNA analysis and the device thereof. The present invention also relates to a method of making rapid, definitive identification of a human or any organism by DNA analysis and the device thereof.

2. Description of Related Arts (a) Identification of Human Leukocytic Antigens (HLA)

Accurate HLA typing is essential for matching donor and recipient in organ or marrow transplantation (4) to prevent the development of acute graft-versus-host disease (GVHD). This is generally accomplished by standard serological typing (2). Recent studies have demonstrated that DNA genotyping can provide more accurate and definitive result (7, 9, 8). Results of HLA-DQ, DR and DP genotyping provided data for accurate matching which is necessary in selecting potential organ donors (3). HLA genotyping using sequence-specific primers polymerase chain reaction (SSP-PCR) amplifications has been previously reported. However, due to highly polymorphic nature of HLA-DQ, DR and DP loci, the number of SSP required will be in the hundreds, and, therefore, exceed the limit of multiplex-PCR for efficient PCR amplification. To ensure the results of HLA genotyping have practical clinical application, multiple of 50 to 100 of separate PCR reactions have to be setup. A kit that is available on the market today includes an amplification process of carrying out a 96 PCR separate reactions, then followed by analysis on gel electrophoresis size separation. This is not only time consuming and costly but prone to error due to the complexity of the reaction setup and sizing uncertainty of the gel electrophoresis. Thus, DNA sequencing is still considered the method of choice for accurate genotyping of the HLA cluster. Unfortunately, because of the existence of highly homologous sequence of pseudogene(s) that may be co-amplified during the polymerase chain reaction (PCR) amplification process, accurate genotyping by DNA sequencing alone may prove more difficult and costly. U.S. Pat. Nos. 5,471,547 and 6,020,187, issued to J.W.O. Tam, disclose a fast annealing process that uses a very inexpensive device for accurate mutation detection, genotyping and fingerprinting analysis. The present invention discloses a method of rapidly analyzing HLA loci of DP, DR and DQ beta sequences by ASO oligo-probes using an improved flow-through format.

(b) DNA Fingerprinting for Rapid Identification of Human Beings and Organisms

DNA fingerprinting by restriction fragment length polymorphism (RFLP) was first introduced in 1985 (12) for human identification, and was subsequently applied to identification of other organisms. In practical applications, DNA fingerprinting has been widely accepted as the best forensic tool for identification of suspects in criminal cases, for paternity disputes and for establishing or verifying the identity of a person. The time consuming RFLP method has been gradually replaced by high throughput automated processes. Using PCR amplification for analyzing the number of short tandem repeat (STR), first discovered in 1991 (11), from 10, 16, 18 or more loci in the human genome, single cell identification is now possible. However, both STR and/or variable number of tandem repeats (VNTR) are relatively expensive because these methods require the use of sophisticated equipment, and labor intensive and time consuming process like the Southern blotting hybridization. Sporadic mutations (10) may reduce the accuracy and the power for definitive identification. Furthermore, STR data suggested that the frequency of mutation, particularly in cancer patients, is not uncommon. Hence, new alternative method is needed. Single nucleotide polymorphism (SNP) genotyping provides greater discriminating power by selecting an appropriate number of SNPs at unlink loci, and the mutation frequency in each locus (site) is lower than VNTR or STR systems for forensic or individual personal identification. This invention presents a method of making rapid, definitive biometric identification of an individual, such as a human being, animal, plant or any organism, using SNP genotyping.

SUMMARY OF THE PRESENT INVENTION

1. HLA Genotyping

Preliminary results suggested that the Allelic-Specific-Oligonucleotide Reversed-Dot-Blotting (ASO-RDB) direct flow-through hybridization is a better alternative for the detection of specific target HLA DNA sequences. The data obtained refer to the specific segments of HLA loci of DP, DR and DQ beta that are able to provide accurate determination of the genotypes. Using one pair of PCR primer and 35 ASO oligo-probes, 83 $DPB_1$ alleles identified by the World Health Organization (WHO) can be effectively classified. Similarly, using one common PCR primer pair and 18 ASO oligo-probes, this simple hybridization protocol can identify the first 2 digit codes of the specific genotypes of the DR and DQ beta loci, enough to distinguish between these major classes of HLA. ASO data are validated by direct PCR sequencing. However, when the same PCR primer pairs are used to perform direct sequencing on the DR and DQ loci, un-interpretable sequencing data occurred frequently. This is because the same pair of primers can also co-amplify highly homologous endogenous pseudogene fragment within the HLA cluster. For this reason DNA sequencing (considered by many as the gold standard) may not be able to guarantee the results for HLA classification. In these cases, to confirm the ASO data, many sets of PCR primers corresponding to each specific HLA types in question were created, and used to perform PCR amplification in separate reactions to create amplicons for sequencing. The positive amplicon(s) were then sequenced. This is the primary reason that direct sequencing may prove to be costly and time consuming. In contrast, the present invention provides a cost effective procedure for HLA identification by using common primer pairs to perform a simple multiplex PCR followed by hybridization with the required numbers of ASO-probes in a Low-Density Array format. The amplified HLA fragments (including the pseudogenes) can be analyzed in a single membrane embedded with the ASO-probes for definitive HLA classification. Hence, this is a far superior method than other DNA or serological methods currently available. Although further detailed classification of the DR, DQ subtypes requires additional oligo-probes when using the direct flow-through method, the number of such oligo-probes is well within the capability of the present format. This invention provides a HLA typing technique which is faster and simpler, does not require expensive equipment, and is therefore less costly to manufacture and operate than direct DNA sequencing and multiplex PCR gel electrophoresis procedures.

The primers and oligo-probes shown in shown in Tables 3-8 have been tested and confirmed to be useful for the classification of HLA genotypes corresponding to the DR, DB and DP genes reported above. Following the scheme presented in FIG. 1 or FIG. 1A, additional primers and/or oligo-probes can be obtained, tested and validated for a more comprehensive genotyping. Although, in the data validating examples, PCR was used for amplification, any method that can produce specific target sequence(s) in sufficient quantity for the ASO-RDB flow-through hybridization analysis may be used. Other appropriate amplification methods or technique is readily apparent to one of ordinary skill in the art reading the teaching herein. Amplification may not be necessary if sufficient quantity of the target sequence(s) can be obtained for the ASO-RDB flow-through hybridization analysis. Detection can be accomplished by labeling of the target DNA or conjugates.

Although HLA genotyping is exemplified in this application, the SNP-based genotyping technique can be applied to other genetic materials and/or sequences obtained from any organism following the teaching of this application, such as the procedures shown in FIG. 1 or FIG. 1A. A flow-through device similar to those described in the U.S. Pat. Nos. 5,741, 547 or 6,020,187, or any new embodiments capable of carrying out flow-through hybridization process can be used.

2. SNP Genotyping

The human genome and the genome of many other organisms have been sequenced and mapped. Within any species, the general DNA sequence information is very similar. However, each species has its own distinct set of genetic information. Hence, many scientists have attempted to characterize disease-related variation among populations. For example, anthropologists use genetic variation to reconstruct human species' history, and to understand the role of culture and geography in the global distribution of human variation. Single nucleotide polymorphism (SNP) data can serve these purposes (12). Brightwell et al. reported the application of SNP genotyping using a simple and rapid single-tube modification of ARMS illustrated by analysis of 6 SNPs in a population of males with FRAXA repeat expansions (15).

The present invention describes the use of allele specific oligonucleotide (ASO) arrays. The number of SNP needed to provide adequate discriminating power is easily attainable by one of ordinary skill in the art following the teaching of this application. The membrane-based microarray ASO-RDB flow-through hybridization format (e.g., see U.S. Pat. No. 5,741,647) may be used to facilitate SNP genotyping. Microarray hybridization format of the present invention produces visible dots which can be analyzed by visual inspection and/ or by using a less costly image analyzer. In contrast, commercially available hybridization format requires high resolution image analyzer for analysis. In principle, SNP of sufficient number may be used anywhere in the genome for discriminating purposes. However, this may compromise the accuracy of paternity and kinship analyses because of the variability of mutation rate in different parts of the genome. Hence, highly polymorphic sites or points in the genome where the mutation rate is relatively low including, but not limited to, the coding region or any regions that satisfy the conditions of relatively low mutation rate may be selected to ensure the inherence nature for kinship identification. Preliminary data obtained using SNPs from 9 highly polymorphic chromosome loci shows that these SNPs were sufficient for SNP genotyping. The number of loci required will depend on the discriminating power required, which is readily apparent to a person of ordinary skill in the art reading the teaching herein. In constructing a polymorphic frequency database for each site, the sequenced DNA samples from 50-150 unrelated individuals is obtained. The kinship analyses of 20 families were performed in parallel with STR Profiler Plus human identity kit, and the results were 100% in agreement. SNP-based flow-through format has proven to be a better alternative for human identification. In addition to data already accumulated and analyzed, expansion of the polymorphic frequency database can be easily accomplished by one of ordinary skill in the art following the teaching of the present application.

3. SNP Genotyping as a Diagnostic Tool

Other than for DNA fingerprinting, SNP genotyping can be utilized for identification of gene fragments, or polymorphism of genes that have altered or attenuated the function of the gene in question. For this reason, the present invention can be used for rapid, definitive identification of infectious agents, inherited disease caused by the specific DNA sequences, or the presence or absence of such infectious agents or DNA sequences that cause inherited diseases.

DETAILED DESCRIPTION OF THE DRAWINGS

FIG. 4 shows a sample data for HLA-DRB and DQB genotyping identification.

Figure 6:
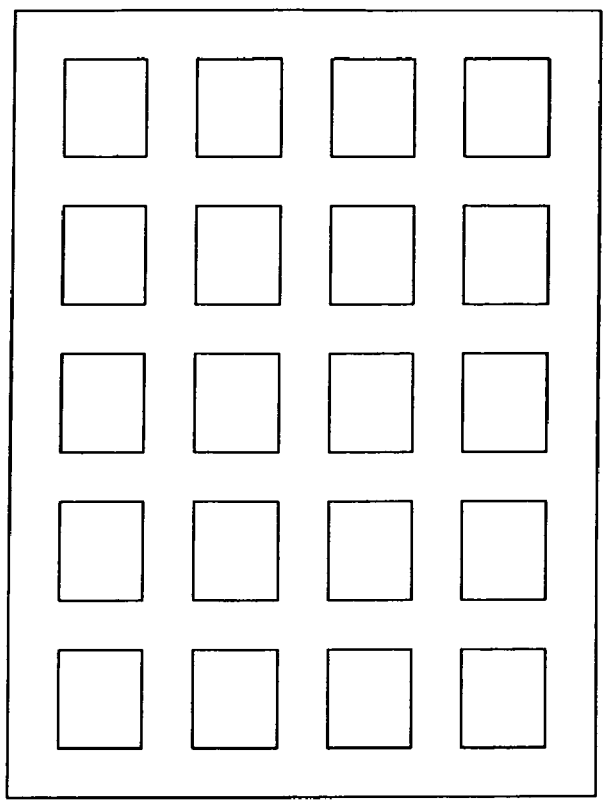
Figure 6:
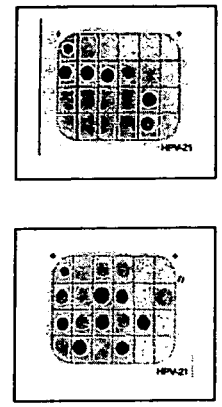

FIG. 6 shows a membrane of the present invention designed for high throughput analyses. FIG. 6A shows a 20-array membrane. FIG. 6B shows the typical images of the 20-array membrane in testing for multiple genes or sequences.

Figure 7:
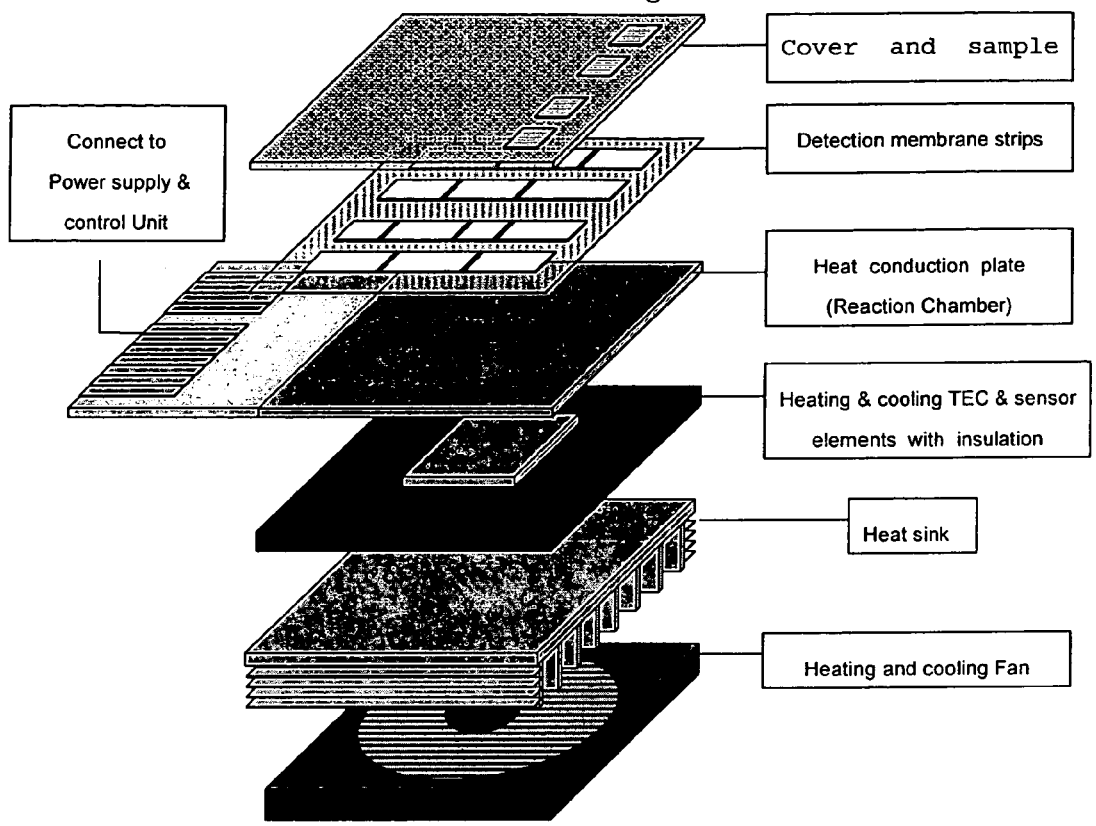
Figure 7:
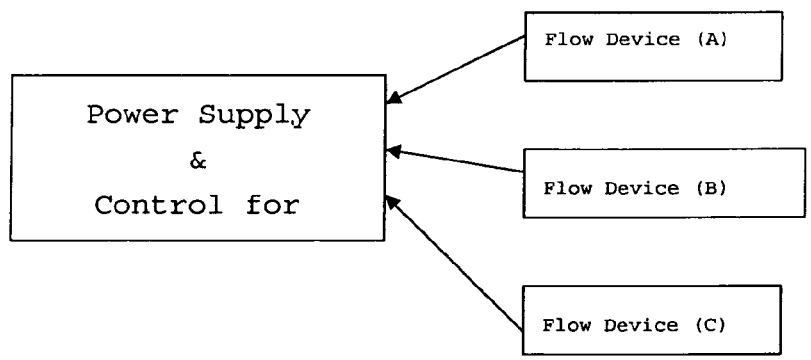

FIG. 7 shows an exploded view of a hybridization device of the present invention, and arrangements of multiple lateral flow-through detection devices connected to a central control unit. In an embodiment, the hybridization device comprises a central controlling unit connected to one or more lateral flow device. The central controlling unit provides power to and controls the lateral flow device where the hybridization process and developing procedures are carried out. Several reactions (or several samples and/or analytes) can be tested simultaneously in a single lateral flow device or in several devices (controlled individually at different conditions) at the same time. The lateral flow device can be in a format of n×m dot matrix (array) or in the form of linear arrays (as shown). Since, during the reaction process, the test solution flows from one end of the array to the other end of the array (i.e., in an east to west, or in a north to south direction), the sensitivity of the detection is increased substantially. The extent of increase in sensitivity depends on the ratio of the total area of the membrane to the area of the dot or line containing the capturing probes. For example, assuming the total area of membrane is 100 mm square, and the dot size is 1 mm square.

In a direct flow-through process (i.e., the solution flows from top surface through the membrane down to the other side of the membrane as in a conventional flow-through process), only 1/100 of the total test solution used will flow through the dot, the location where the target molecule will bind to the probe(s) immobilized on the membrane. However, if a lateral flow-through process is used, the sensitivity is only dependent on the ratio of the width of the dot to the width of the membrane (i.e., the cross section of the membrane) For instance, in a lateral flow-through process, the total amount of solution that will pass through a 1 mm dot provided on a 10 mm×10 mm membrane will be about 1/10, which represents a 10-fold increase in sensitivity using the same amount of target analyte (test solution containing the target molecules). When a line array format is used in the lateral flow-through process, the sensitivity will be further increased since all the target molecules will pass through the line extending across the strip (or membrane) . The lateral flow-through process allows quantitative measurements to be taken during the hybridization process because the flow of the analyst is more uniform.

Figure 8:
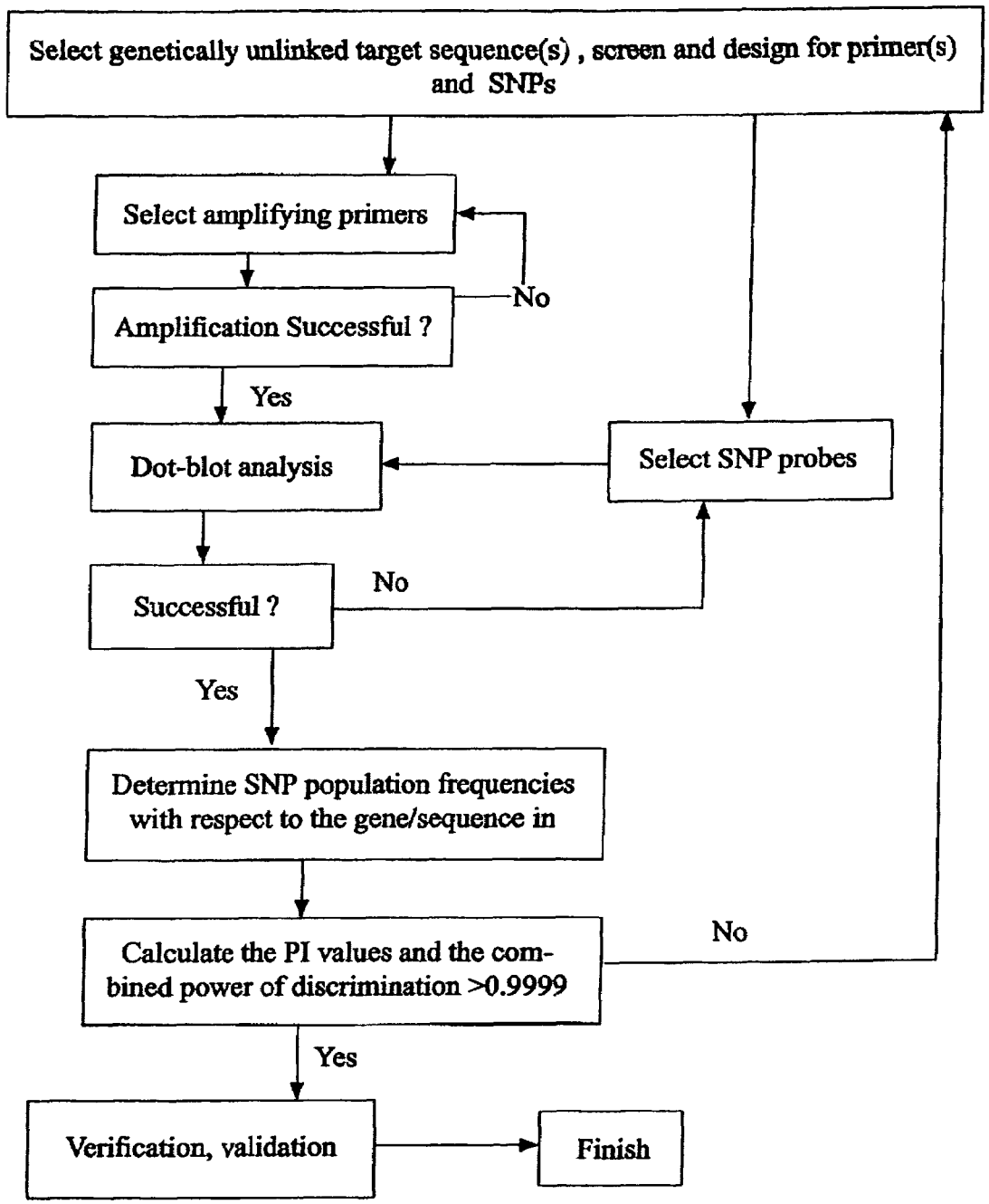

FIG. 8 shows a method of the present invention for constructing a SNP database.

Figures 9, 10:
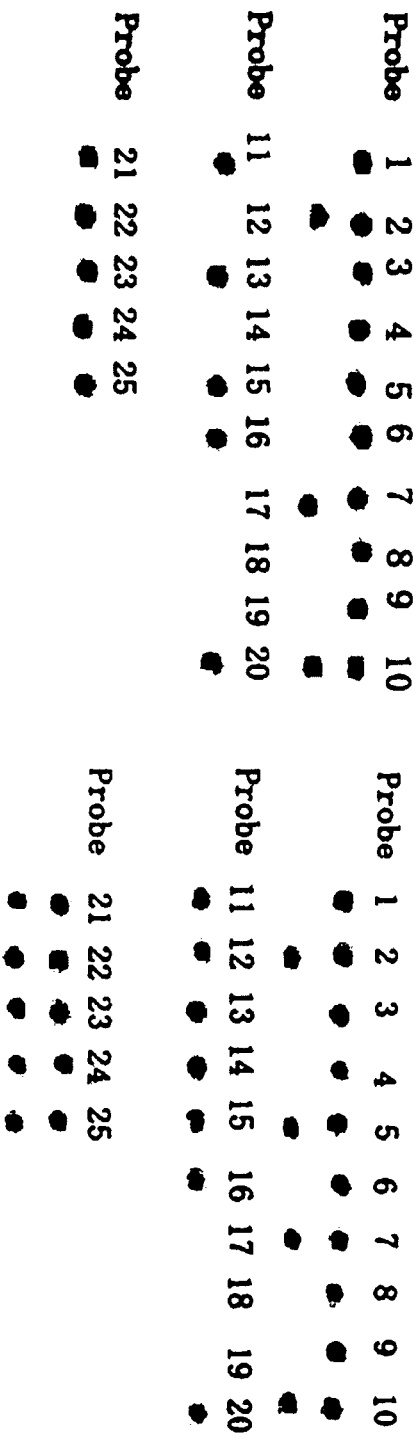

FIG. 9 shows a sample data for identification of a human being or an organism using SNP genotyping.

FIG. 10 shows the loci used for the method in the FIG. 8.

FIG. 11 shows a HLA-DPB1 genotyping results based on samples obtained from a Chinese population (Table 1).

FIG. 12 shows HLA-DPB1 allele and genotype frequencies for a Chinese population (Table 2).

FIG. 13 shows the ASO Oligonucleotide probe sequences identifying the respective HLA genotypes, and the PCR primer sequence pairs for amplify the corresponding fragments for analysis.

The present invention will be described in connection with preferred embodiments, however, it will be understood that this is no intent to limit the invention to the embodiments described. On the contrary, the intent is to cover all alternatives, modifications, and equivalents as may be included within the spirit and scope of the invention as defined by the appended claims.

DETAILED DESCRIPTION OF THE INVENTION

1. HLA Genotyping

The following describes a method of the present invention for obtaining the HLA genotyping ASO probes and PCR primers from genomic sequence database, and for performing HLA genotyping analysis:

1. Select Appropriate Gene Segments and Determine Appropriate PCR Primers and ASO Sites 1.1. Select appropriate target sequence(s) to be analyzed by screening data from GenBank and/or by performing population screening by sequencing target genes or DNA segments to obtain SNP or ASO profile appropriate for HLA genotyping.

A method of the present invention for selecting appropriate target sequence(s) is detailed below:

1.1.1. Find all the HLA DNA sequence data from GenBank according to their individual class (i.e., Class I or Class II) and subtypes (i.e., DR or DQ or DP, etc.). Align HLA DNA sequences based on individual classes and subtypes to determine the most polymorphic region(s) that will be appropriate for use in HLA genotyping.

1.1.2. Within polymorphic region(s), identify PCR primer pair(s) that is conserved among the subtypes of interest so that when using these primers, the PCR products can always be amplified for all the subtypes of interest for further analysis using the flow-through hybridization process.

1.1.3. To validate the usefulness of these primers, PCR amplification is performed using a large number of random samples to obtain statistically satisfactory data for positive amplification of the region(s) in question, and to ensure that any drop out of any allele does not result due to false negative amplification process. In addition to statistical validation, internal control(IC) is included to ensure that an inhibitor of PCR is not present in the test sample which will prevent the PCR amplification reaction. The design of IC (may be 1 or more) will depend on the test required. In the case of HLA and SNP fingerprinting, and genotyping of genes responsible for genetic diseases, the nature of IC sequence will be non-homologous to the human genome in question (i.e., a sequence totally unrelated to sequence in question). Since human cells are mostly diploid (except germline) genome, the concentration issue is much simpler because theoretically the concentration of the test loci should be either 1 (homozygous) or 0.5 (heterozygous). Hence, two different sequence fragments flanked by the same PCR primer sequences can be used for IC. This means that using a fragment different from that of the target fragments to be analyzed, one can use loci of known character of homozygous and heterozygous sequences within the fragment (that is two different probes (1 homo; 1 hetero)in the fragment) as probes so that these IC concentration ratio can be calculated. Since the PCR amplification does not affect the relative concentration, the ratio of signal will be 2:1 theoretically. Any fluctuation will be seen as the hybridization efficiency. The two ICs with a ratio of 2:1 serves as the reference for homozygous and heterozygous, respectively, for the loci in question. If the observed result indicates only one allele, and the concentration in question is equal to or less than 0.5 of the homozygous IC or close to 1 compare to the heterozygous IC, the possibility of loss of heterozygousity should be investigated, meaning: may be one of the two chromosomes has lost or could not amplify. The expected result of ONE dot is homozygous which indicate the two chromosomes are the same, and therefore the concentration should be closer to the homozygous IC than that of the heterozygous IC. Hence, ICs will be important for obtaining accurate results since clinically dependable result is crucial for any diagnostic test.

Additional information on DNA data bank and alignments can be found in the reference section of this application (see Reference No. 5-6).

1.1.4. The procedures described herein for HLA genotyping can also be adopted by one of ordinary skill in the art reading the teaching herein for genotyping of other genes or DNA sequences of interest, or for determining SNP profiles for DNA fingerprinting/identification process performed in combination with flow-through hybridization process.

1.1.5. To maximize the efficiency of PCR amplification, the fragment length of the ASO probes is normally selected or kept as short as possible, preferably to within a few hundred base-pairs. If suitable primer pairs cannot be identified, adjustments on the components in the PCR reaction mixtures and the PCR processes, i.e. the PCR program, can be made to optimize the amplification reaction to ensure the production of amplicons during development of the genotyping process. Such development processes are apparent to persons of ordinary skill in the art after reading the teaching herein. In some cases a totally conserved sequences for PCR Primer cannot be found and degenerate primers or multiple primers for the same loci may have to be use. In these cases, appropriate adjustments to the PCR conditions are made to ensure that all loci will not be missed.

1.1.6. When unique region(s) for successful subtype differentiation cannot be identified, multiplex PCR may be required. The primer pairs are designed to Tm values within the operable range for successful annealing during the amplification process. As used herein, "Tm" means, for example, the temperature of the reaction where the concentration of DNA molecules in double strand as well as single strand is equal. Hence, at higher temperature more double strand DNA will become single strand, and conversely at lower temperature, more single strand molecule will anneal into double strand. For a given population where sequence data is not available, a population screening by direct DNA sequencing is usually performed. For example, a screening of a sample Chinese population was performed as follows: (a) Random samples of over a hundred subjects were amplified by PCR using two pairs of primers, followed by hybridization using the ASO Probes designed based the procedures described in the following sections. (b) The results were confirmed by DNA sequencing.

1.2. Using the data obtained above, the ASO sites to be used for genotyping are determined and selected. Determine whether the sites selected are indeed unique for HLA typing within a population using data obtained from GenBank or generated by sequencing random samples. The procedures for designing ASO probes and for validating the uniqueness of the probes are as follows:

1.2.1. From the selected region(s) of the alignments for which satisfactory polymorphism among the subtypes are found, further search for a unique 20-30 nucleotide sequence or fragment is performed. The unique sequence or fragment is used as an allele specific oligonucleotide (ASO) probe to capture the amplified target by hybridization process in order to detect the presence of such unique HLA subtype. As used herein, "unique sequence or fragment" means, for example, that the sequence or fragment is completely homologous to only one sequence, among these subtype sequences.

1.2.2. To verify that the ASO probe(s) is unique, the sequence is matched with all human DNA sequence data which are available in the GenBank or in its European equivalent to determine if indeed the ASO probe has 100% match with ONLY the HLA subtype of interest. This will ensure that at least (until new sequences are discovered) among the available data, the ASO probe(s) is unique for a given region.

1.2.3. Since PCR fragment length is kept short to improve the efficiency of amplification, one ASO probe may not be sufficient to provide a definitive differentiation to determine the unique subtype. Hence, a set of multiple ASO probes within one PCR fragment and/or in different fragments using the multiplex PCR may have to be used to give a definitive genotyping classification. In this case, a specific pattern of the ASO array will be generated by the hybridization process for each of the given HLA subtypes. After thorough analysis of the data, the ASO sequences undergo validation using random human DNA samples.

Figure 2:
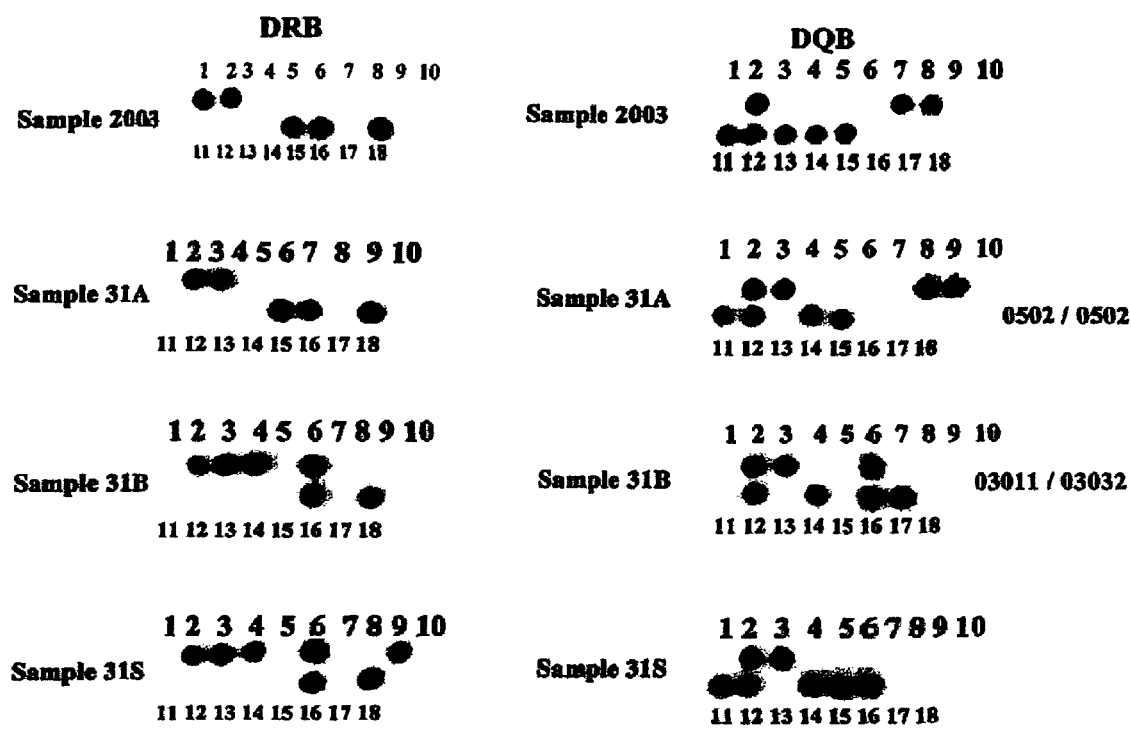
FIG. 2 shows a HLA-DQB genotype ASO detection profile obtained using a method of the present invention.
Figure 3:
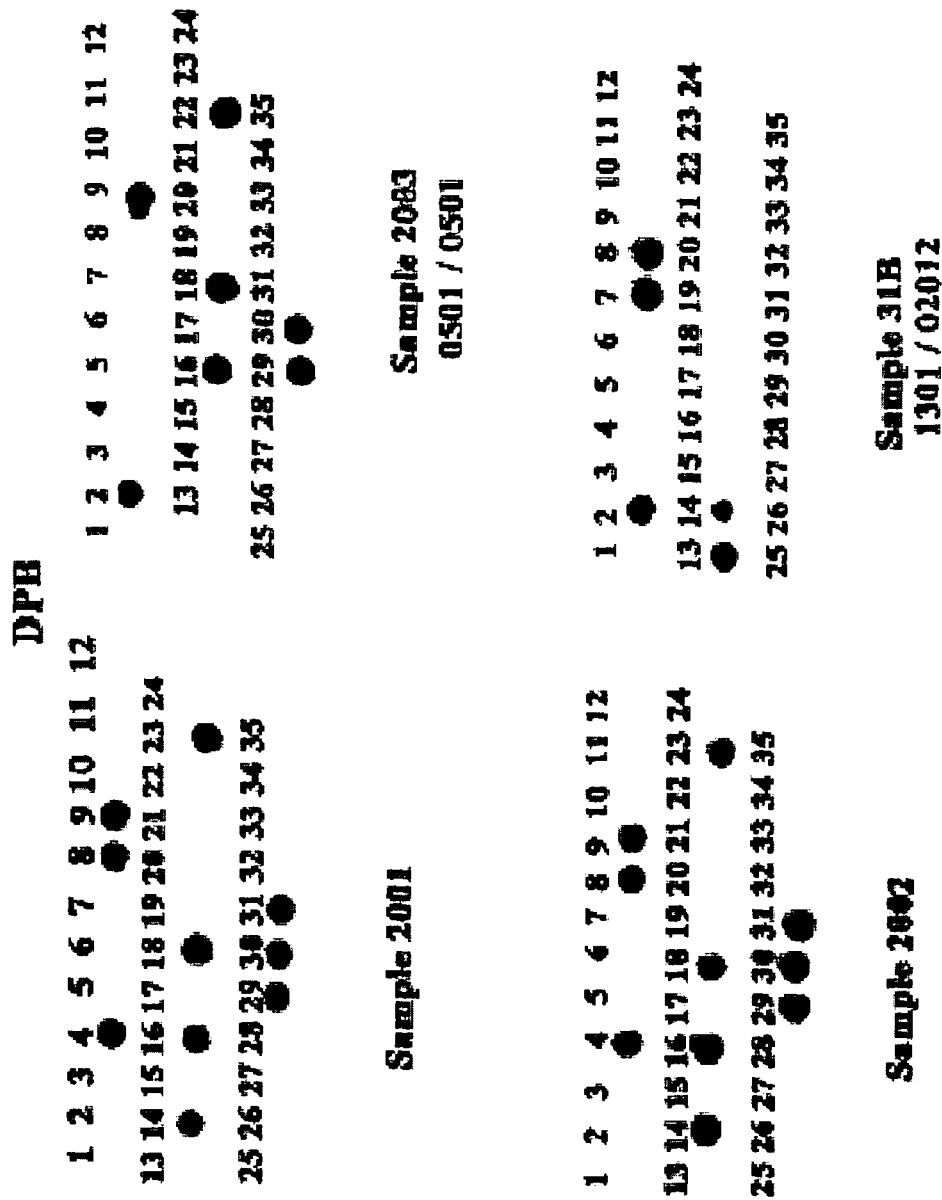
FIG. 3 shows a HLA-DPBL genotype ASO detection profile obtained using a method of the present invention.

1.3. After the number of ASO capture probes is finalized for use, the array patterns for each of the genotypes are determined. Examples of specific array profiles are shown in FIGS. 2 and 3. The array profiles shown in FIGS. 2 and 3 were developed for determination of HLA DRB, DQB and DPB subtypes using 18 ASO probes and 35 ASO probes, respectively.

Similar procedures can be used for other genes and genetic materials from other organisms. The primer sequences and the number of ASO probes vary for different genes and for different applications. For example, human identification may require a 50 or more ASO array to obtain definitive identification (see FIGS. 3 and 4). The detection format can include an array of dots or linear lines depending on the configuration of the flow-through hybridization device.

2. Performing ASO-RDB Detection 2.1. ASO oligonucleotides are immobilized on a membrane or any suitable matrix for capturing the target loci. As used herein, "membrane" means, for example, any suitable matrix material capable of immobilizing ASO oligonucleotide probe(s) and porous enough for test solution containing the target nucleic acid molecules to pass through freely. In an embodiment, the membrane or matrix may be constructed of Nylon, NC, Biodyne, Porex, porous metal or durable gel matrixes.

Immobilization of the target sequence (or loci) can be achieved by covalent bonding, non-covalent (i.e., electrostatic, hydrophobic or any other interactions including UV cross-linking) interactions, or interactions through mediators such as receptors or antibodies. The membrane as shown in FIG. 2 and 3 is Biodyne C using EDC to form covalent linkage between the membrane's COOH and the terminal $NH_2$-modified end of the ASO probes. Avidin-biotin linkage or ASO poly-T tailing for UV cross-linking is equally effective.

2.2. Target sequences are amplified using appropriate primers to generate enough amplicons to enable adequate analysis. The target molecules can be appropriately labeled for signal generation according to the method of signal detection used for final analysis. Labeling can be performed on one or both of the primers by covalent linkage of the label molecule at the 5'end or using one of the four dNTP labeled nucleotides during the PCR amplification process for extension labeling of the newly generated amplicons. The label molecule can be of any kind as long as the signal can be monitored and developed. Biotin coupled with avidinenyzme conjugate can be used for color detection. Other suitable labeling systems including, but is not limited to, colloidal gold conjugate and fluorescence label, magnetic particles conjugate, quantum dots, chemiluminescence label molecules, or other suitable systems already developed or to be developed, may be used as well.

2.3. ASO profile analyses are performed using flow-through hybridization process such as the method described in U.S. Pat. No. 5,741,647. Hybridization is performed in the hybridization chamber with ASO capture probes coupled to the membrane. An ASO profile analysis is described below:

a) Denaturing and contacting solution containing target DNA or sequence with membrane;

b) Washing membrane with washing (or SSC or blocking) solution, preferably three times; and c) Developing color for visual inspection or spectrometric measurements. For quantitative measurements, one can use a scanner and imaging software to perform the analysis. Alternatively, target DNA or sequence can be labeled with fluorescence dye and analyzed using a spectrometric imager immediately after the washing step.

2.4. The results are compared with known sequence data to ensure accuracy of genotyping assay.

2.5. Probes and testing conditions are further modified to improve the accuracy of genotyping assay, and RDB-ASO data is verified by DNA sequencing.

3. Validation

Validation is performed using random samples. A validation procedure of the present invention is described below:

3.1. As mentioned above, once the primers pair(s) and ASO capturing probe(s) are immobilized on a membrane, random DNA samples of sufficient number are used to perform PCR amplification. Hybridization of target sequence(s) or amplified and labeled DNA products or molecules is performed to generate an ASO array pattern.

3.2. HLA subtype and corresponding DNA sequence(s) are determined from ASO probes.

3.3. Corresponding PCR samples are prepared for direct DNA sequencing.

3.4. Agreement of the results obtained from DNA sequencing and from flow-through array is needed to validate the HLA genotyping assay. Samples for validating genotyping assay can be obtained from any randomly selected individuals. Once the samples have been obtained, true genotyping can be performed by DNA sequencing as stated in section 3.3. If sequencing data agree with those obtained from flow-through array, the validity of the data is confirmed. Further validation of genotyping assay can be performed through field tests, such as testing random samples, analyzing data and comparing statistically values such as sensitivity, specificity, positive predicted value or negative predicted value, at independent laboratories to evaluate the accuracy of genotyping assay.

II. SNP Genotyping

The following is a method of the present invention for constructing a SNP database and developing a SNP genotyping assay:

1. Select SNP sites and determine the power of exclusion. As used herein, "power of exclusion" means, for example, the accuracy of the method in differentiating people or organisms. For instance, power of exclusion of 1 in 10 billion or 100 billion means that when using a selected number of SNP sites one can only expect to find two identical individuals in screening 10 or 100 billion individuals, respectively.

1.1. Select appropriate SNP oligonucleotide probes for capturing specific target sequences to be analyzed either by screening data from GenBank or by performing population screening, i.e., direct DNA sequencing of target genes or target DNA segments, to obtain SNP profile and population frequencies.

1.2. From these data, identify the SNP sites to be used for fingerprinting based on polymorphic frequency, and determine whether or not the selected sites are indeed hot spots for mutation within a population by sequencing the samples obtained from random population screening.

1.3. Determine the number of SNP probes required, and calculate total heterozygosity to determine the power of exclusion with the given number of SNP points used for the analysis profile pattern (i.e., the SNP dot array as shown in FIG. 9).

Power of exclusion depends on the number of SNP in a given loci. For example, in a given loci, if 2 different bases, e.g., G and A, are found in a sample population at 50% each. The probability is ½. If 50 of such sites can be found (these sites are randomly distributed and are not linked to each other in the chromosome) the differentiation power will be ½ to the power of 50.

2. Perform SNP profile pattern (a combination of SNP array showing the array of corresponding genotypes in each loci of that individual) detection 2.1. Design appropriate primers for amplification, and select appropriate SNP-probes for hybridization detection after the loci are screened and selected as described above.

2.2. Amplify target sequence(s) and perform SNP profile analyses using flow-through hybridization process such as the method described in U.S. Pat. No. 5,741,647.

2.3. Compare the data obtained in section 2.2. with known sequence data to evaluate the accuracy of the SNP genotyping analysis.

2.4. Modify SNP probes and testing conditions to improve the accuracy of the SNP genotyping analysis. RDB SNP data are verified by DNA sequencing.

3. Validate the method with random samples.

Other advantages and aspects of the present invention will become apparent upon reading the following examples.

EXEMPLIFICATION

The invention being generally described, will be more readily understood by reference to the following examples which are included merely for purposes of illustration of certain aspects and embodiments of the present invention, and are not intended to limit the invention.

Example 1

The following procedures were used to determine HLA genotypes of 140 human samples obtained from a sample Chinese population. The results were used to develop a kit for rapid classification of HLA subtypes of the first 2 digit codes corresponding to WHO nomenclature. In an embodiment, a kit can be designed to cover HLA-DR, -DQ and -DP alleles which are typically used for tissue matching between a donor and a recipient prior to organ transplantation.

Test Procedures:

A) Isolation of DNA

The following protocols are recommended, but alternative procedures which are readily apparent to one of ordinary skill in the art and which are equally effective may be employed. Nucleated cells such as WBC or tissues are washed with PBS, centrifuged, and the supernatant is removed. The pellet is resuspended in 200 µl PBS. DNA extraction is performed with QIAamp DNA mini kit (QIAGEN) following Blood and Body Fluid Spin protocol as re-commended by the manufacturer. Other commercially available kits for isolating DNA may also be used. However, DNA isolation procedures that produce purified DNA that do not contain DNA polymerase inhibitor are crucial to ensure efficient amplification. Elute DNA in 50-200 µl Buffer AE and store at −20° C. until use.

B) PCR Amplification

Since PCR is extremely sensitive process, special care must be taken to prevent cross contamination and/or to prevent false positive results. Hence, the following guidelines should be observed: Wear surgical gloves at ALL TIMES when performing PCR procedures. Preferably, prepare PCR reaction mixtures in a pre-PCR area or a clean PCR preparation station where no amplification products are present. PCR reaction and hybridization should be performed in separate areas. For example, hybridization should be performed in a post-PCR area.

Use 70% ethanol and paper towel to clean the working bench/area. Use 70% ethanol and paper towel to clean all the pipettes before starting PCR amplification. Use filtered/sterile tips for ALL pipetting steps. NEVER reuse any tips.

PCR is just one of the many techniques which can be used for amplification. Other amplification techniques, which are readily apparent to one of ordinary skill in the art, such as various methods for isothermal amplification using appropriate primers to amplify target sequence(s) to obtain sufficient quantity of target sequence(s) (or DNA molecules) to carry out flow-through array detection may be used.

PCR reactions are performed using, for example, commercially available polymerase AmpliTaq™ Gold (Applied Biosystem). Five primers pairs (1 pair used for amplifying the DR genes, i.e., forward primer DRB-F1: 5'-ATCCTTCGTGTC-CCCACAGCACG-3' [SEQ ID No. 97] and the reversed primer DRB-R1: 5'-GCCGCTGCACTGTGAAGCTCTC-3' [SEQ ID No. 98]; 1 pair used for amplifying the DQ genes, i.e., the forward primer is DQB-E2-F2: 5' CGGTGATTC-CCCGCAGAGGAT-3' [SEQ ID No. 99] and the reversed primer is DQB-E2-R2: 5'-CCACCTCGTAGTTGT-GTCTGC-3' [SEQ ID No. 100]; and 3 pairs used for amplifying the DP gene, the forward primers [SEQ ID NOs. 101-103] and the reversed primers [SEQ ID NOs. 104-106]) listed in Tables 4, 6 and 8 (below) are individually 5'-end labeled with biotin. Other appropriate labeling methods described above can also be used. In 25 µl reactions, prepare a PCR master mix as follows (This example is intended to illustrate one particular program for PCR amplification reaction of the present invention. If other SNP primer sequence(s) are used, the condition for PCR and hybridization must be optimized):

|  | Each reaction (µl) | 10 reactions |
| --- | --- | --- |
| PCR-Mix | 19.00 | 190.0 |
| DNA Taq Polymerase | 1 ul (1 unit) | 10 ul (10 units) |
| DNA Template | 5 (~100 ng) | — |
| Total | 25 | 200 |

Amplification program was optimized using PE 9700 thermal cycler:
For PE 9700 (or MJ thermal cycler):

| | | |
| --- | --- | --- |
| 95° C. | 5 min | |
| 95° C. | 20 sec | ⎤ |
| 55° C. | 30 sec | ⎦ 40 cycles |
| 72° C. | 30 sec | |
| 72° C. | 5 min final extension | |

When using different primers or other thermal cycler, modifications to the cycling program may be required.

C) Quality Control for PCR

It is important to have a positive control and a negative control in every PCR analysis. Positive control is needed to demonstrate the efficiency and specificity of PCR, and negative control is needed to determine whether PCR reagents are contaminated. Internal controls are also needed to provide proper interpretation, and to ensure the dependability and accuracy of the data. The type and the number or IC depend on the type or nature of the test needed.

IC can be used to track each step of the hybridization reaction or procedure. For example, IC can be used to determine whether a sample was added or whether any inhibitors are present in a sample which will prevent PCR reaction from working properly. IC can also be used to track the efficiency of the reaction, or to determine the concentration of target molecule in a semi-quantitative or quantitative manner.

If a quantitative or semi-quantitative measurement is needed, the detection array or membrane can be prepared with a signal generating internal control (IC) onto the membrane to provide a detectable signal at predetermined concentrations when a preprogrammed or predetermined condition has been met. In such embodiment, the IC is developed simultaneously with the test samples after hybridization. In another embodiment, additional IC can be added into the PCR reaction mix to indicate the intrinsic PCR efficiency. This can serve also as an internal control to indicate the presence or absence of inhibitor within the PCR reaction.

The IC system in the PCR reaction mix of the present invention provides several advantages. Since the PCR reaction is carried out in the same reaction tube, the absence of IC and test sample signal indicates the presence of an inhibitor. If the same primer sequences for IC and test samples are used for the PCR amplification, it can serve as an intrinsic control for PCR reaction efficiency. IC can also be used to determine the detection limits or cut off value of the PCR reaction and/or the efficiency of the hybridization process, and to provide an indication of whether hybridization was successfully completed. In addition, IC can be used to determine whether reagents for signal development are acceptable or prepared properly, and whether proper procedures were followed during hybridization.

D) Hybridization

Preparations Prior to Hybridization:

1. Pre-warm hybridization solution (i.e., 2×SSC or any commercially available solution/product) to 42° C. in a water bath before use. If precipitate is present in solution B (SSC+0.5% SDS), dissolve the precipitate by incubating solution B at 42° C. until the precipitate is dissolved. Keep the temperature at 42° C. through out the hybridization process to maintain set stringency.
2. Prepare NBT/BCIP working solution by dissolving a tablet in 10 ml of solution C or PBS buffer (phosphate buffer saline). Protect the diluted working NBT/BCIP solution from light and store any unused solution at 4° C.
3. Equilibrate hybridization solution (2×SSC+0.05% tween 20) to room temperature.
4. Denature all biotinylated PCR products by heating at 95° C. for 5 min, and then chill on ice immediately for at least 2 min.

Hybridization Set-Up

1. For the flow through hybridization studies, one can use the direct flow through device described in U.S. Pat. No. 6,020,187 or a lateral flow device described in this application. For the genotyping of HLA in this example, a direct flow device is used. Switch on hybridization device to preheat at 42° C. filled with distilled water.
2. Place the detection membrane(s) which are embedded with capture probe(s), such as those listed in the sequence listing below, in the hybridization chamber. Secure the membrane(s) with, for example, a cover lid.

Hybridization of PCR Products

1. When the temperature reaches 42° C. (±0.5° C.), deliver 1 ml of the pre-warmed hybridization solution for pre-hybridization to cover the membrane. Incubate for at least 2 minutes with the cover closed to prevent heat loss during pre-hybridization. This is to ensure temperature equilibrium at the set temperature.
2. Add 0.5 ml of the pre-warmed hybridization solution to each denatured PCR products separately for testing, and add the DNA samples into designated well. Contacting DNA samples which contain the target sequence(s) with membrane surface and incubate at 42° C. for 5 minutes, and then allow DNA samples which to flow through the membrane. Hybridization is normally completed within 30 seconds. The 2-5 minutes incubation period ensures that the temperature of the DNA samples will reach the set temperature.
3. Wash the membrane with 3×0.8 ml of hybridization solution.

Color Development
1. Set temperature to 37° C. Start pump, and immediately begin dispensing 0.5 ml of blocking solution. Stop pump. Add another 0.5 ml of blocking solution and incubate for 5 min, then pump out the solution.
2. Turn off pump and add 0.5 ml of the enzyme conjugate. Let the membrane sit for 3 min. Color development works well between 25-37° C. Start pump. Wash the membrane thoroughly, preferably four times, with 0.8 ml of buffered saline solution at pH 7.4.
3. Turn off pump and add 0.5 ml of the NBT/BCIP solution (from Roche).
4. Cover lid. Incubate for about 5 minutes or until color develops. Note: DO NOT incubate for over 10 minutes.
5. Turn pump on to remove NBT/BCIP solution. Wash the membrane, preferably three to four times, with 1 ml of solution B after the color has completely developed. Rinse membrane with 2 ml of dH$_2$O once.
6. Inspect results as soon as possible, preferably within 1 hour, by direct visualization, or scan the image for semi-quantitative detection.

Result Interpretation

Figure 1:
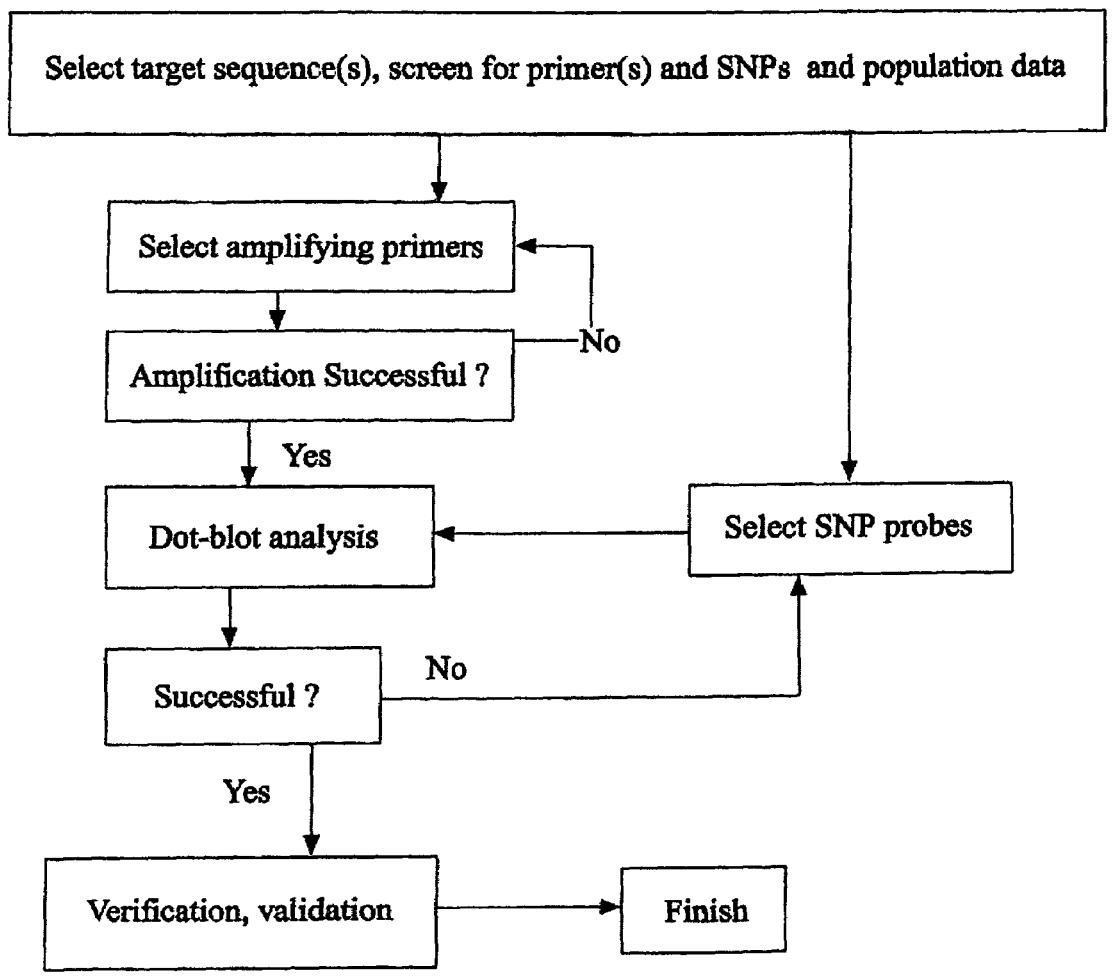
FIG. 1 shows a method of the present invention for constructing an ASO probe and PCR primer database.
Figure 1A:
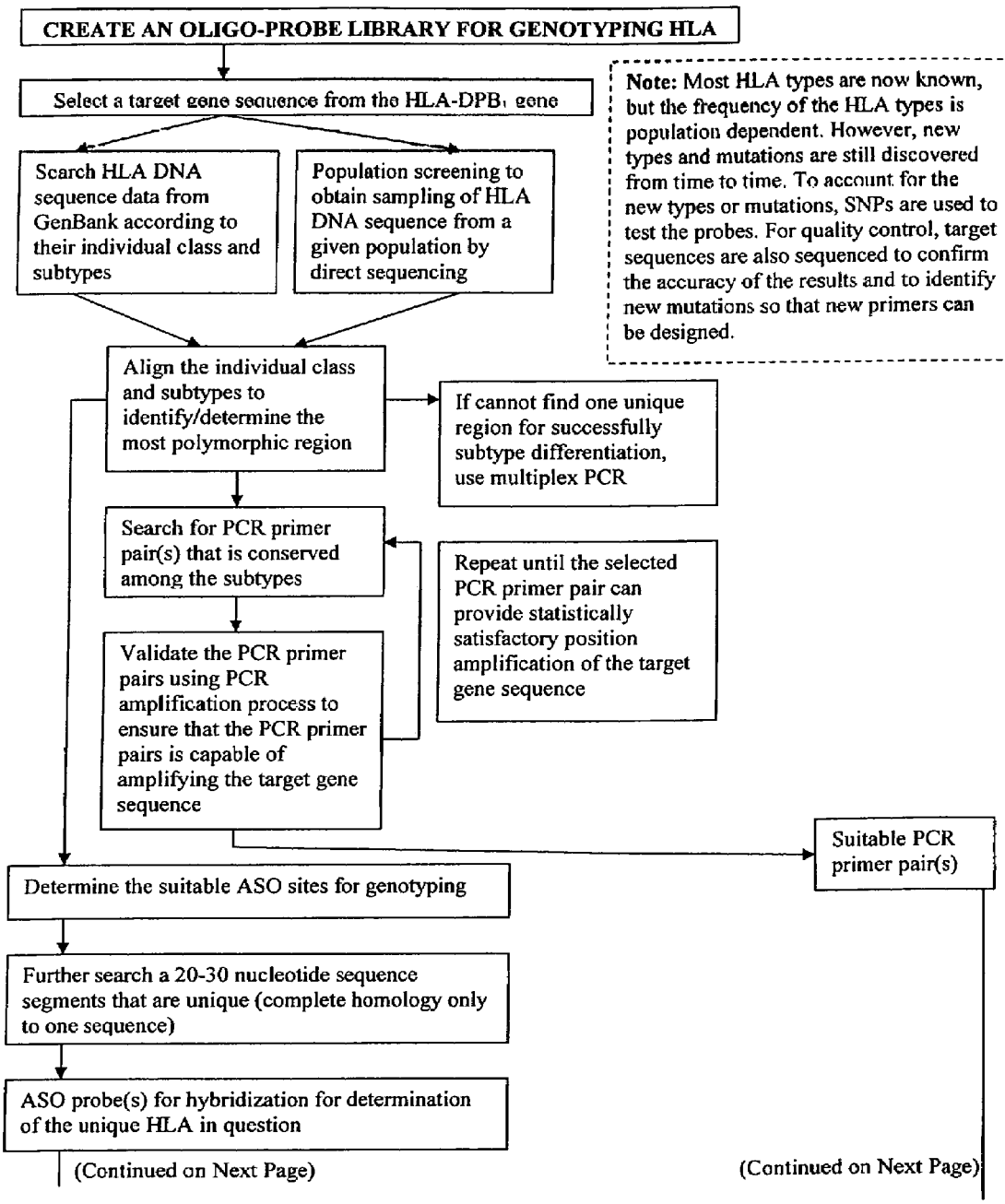
FIG. 1A shows a method of the present invention for building an Oligo-Probe Library for HLA Genotyping.
Figure 5:
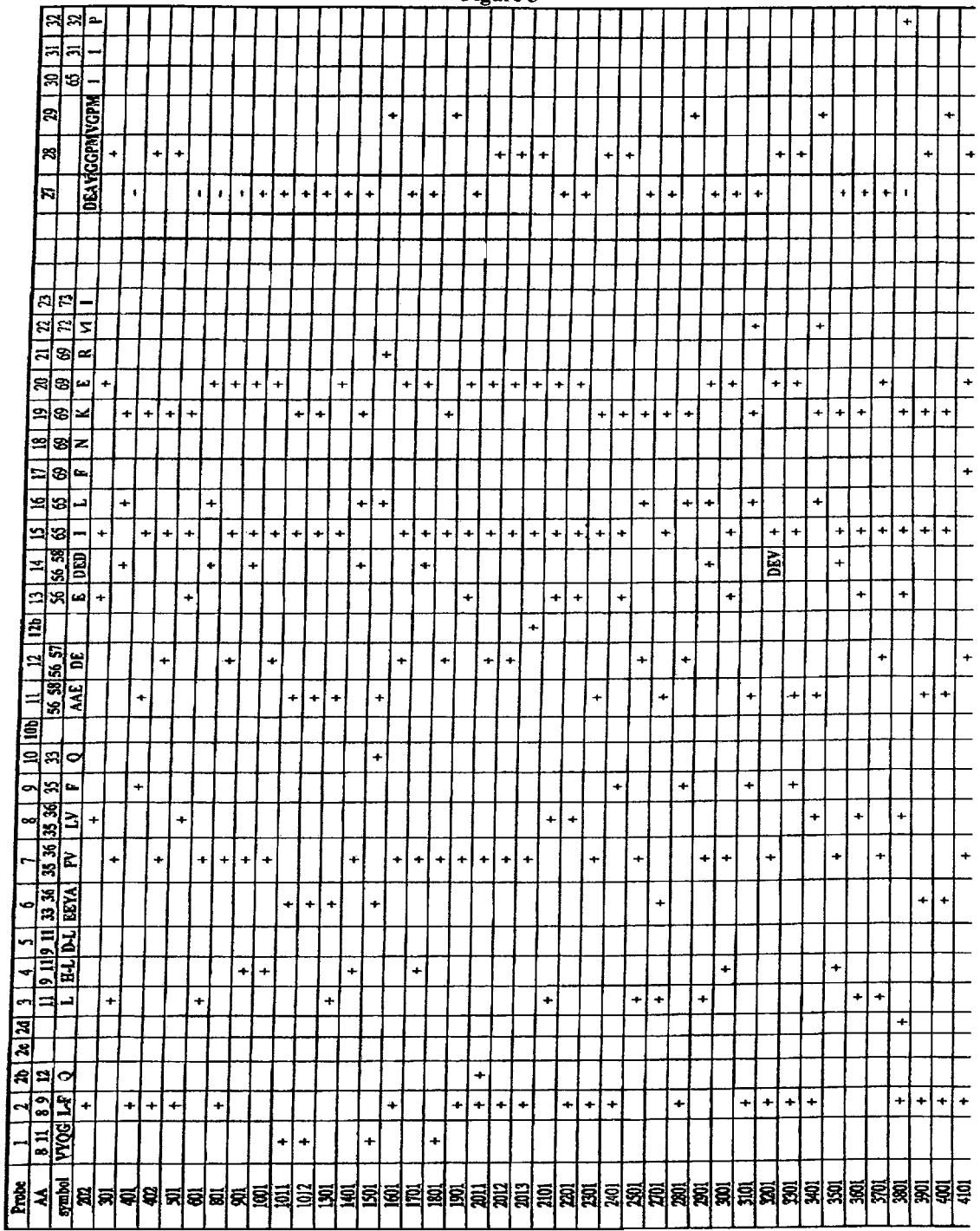
FIG. 5 shows a sample data for HLA-DPB genotyping identification.

The presence of a clearly visible dot indicates a positive result. A total of 96 ASO probes (DRB: 29; DQB1: 24 and DPB1: 43), corresponding to SEQ ID 1-96 in the sequence listing for the HLA cluster, and five PCR primer pairs, corresponding to SEQ ID NO 97-106 in the sequence listing for amplification had been designed according to the scheme in FIG. 1 and 1A. The ASO probes and primer pairs have been evaluated and determined to be suitable for the classification of the HLA DR, DQ and DP genes. FIG. 2 shows the typical results of HLA-DRB and DQB loci using 18 ASO probes each respectively and the classification into genotypes labeled in each of the array profile patterns. Similarly, FIG. 3 shows the results for HLA-DPB1. In this gene, 35 ASO probes of 43 designed (32 probes were finally adopted after screening and validated from random samples) were used in generating the array profile pattern. ASO-HLA DR, DQ and DP data summary are given in FIG. 4 and 5. Genotypes and allele frequencies are given in Table 1 and 2. All data obtained from reversed dot blot array by flow through hybridization (which used a total of 141 random human samples) were separately confirmed with DNA sequencing. In principle, any known ASO (or SNP) oligonucleotides of any organisms with adequate data to perform genetic analysis can be tested, identified or detected by the rapid, genotyping flow-through hybridization method of the present invention. Hybridization results are obtained within minutes, which translate into at least a ten-fold increase in speed over conventional hybridization techniques.

Example 2

Simplified Genotyping Protocols and Devices

The flow-through DNA hybridization method and device as described in the U.S. Pat. Nos. 5,741,647 and 6,020,187, respectively, reduces hybridization time from many hours or days to minutes (the whole hybridization assay can be completed in 5-30 minutes depending the method used to generate detection signal). The device is also inexpensive to manufacture, and uses 10 times less reagents than convention hybridization devices which will lead to more affordable DNA diagnosis technology.

The present invention provides an inexpensive platform for studying the nucleic acids, proteins and other chemical interactions using a low-density array format. This invention further provides a method of genotyping complex HLA systems. As illustrated above, the genotyping method of the present invention has been shown to provide significant improvements over conventional hybridization processes, even the hybridization process as described in U.S. Pat. Nos. 5,741, 647 and 6,020,187.

The present invention further provides additional improvements over existing flow-through hybridization techniques. For example, the hybridization device of the present invention includes a detection membrane, such as the membrane shown in FIG. 6 in a 4×6 array format. With the use of the ELISA 96 wells format, in which each well can be prepared with a 5-dot matrix array, for processing 96 samples and 5 different analysts to simultaneously. This increases the analysis throughput substantially.

The array format may be adapted by one of ordinary skill in the art to accommodate additional wells for analyzing a larger set of nucleotide sequences rapidly and inexpensively. The hybridization device of the present invention is a breakthrough in rapid DNA diagnostics. A lateral flow and miniature embodiment of the device of the present invention is depicted in FIG. 7.

Significant improvements on the hybridization protocols are also disclosed which include:

(i) Elimination of the prehybridization step in which the blocking and hybridization steps are combined using an improved reagent mixture (i.e., DNA samples are placed in hybridization solution and flow-through detection membrane without pre-hybridization)

(ii) a single-step hybridization process in which the target sequences or molecules are labeled with fluorescence tags, quantum dot, colloidal gold particles, magnetic particles or other appropriate labeling tags to eliminate the enzyme-link conjugate substrate color development step. These improvements will enable a technician to complete the entire hybridization process in 5 minutes or less. Hence, the method of the present invention should provide further savings in terms of time and reagent cost.

Example 3

SNP Genotyping

Eight gene clusters and 55 segments from 50 to 400 individual samples were sequenced to identify sites suitable for SNP genotyping. FIG. 9 shows one of the panels which were used for fingerprinting. Results were compared with STR Profiler Plus fingerprinting kit (Applied Biosystems, Inc.) to ensure accuracy. FIG. 10 shows the loci used in the fingerprinting method as shown in FIG. 8. Other probes and primers for other candidate genes/sequences may be readily determined by one of ordinary skill in the art following the teaching of this application. Genes which have been tested include Globin genes for Thalassemia, BRCAs, ApoE, Collagens, p53, G6PD deficiency alleles and HLA DP, DQ and DR. Any known SNPs of any organisms with adequate data to perform genetic analysis can be tested or detected using the rapid SNP genotyping process of the present invention.

To identify the DRB genotypes, the PCR were carried out with the primer pair of DRB-F1: 5'-ATCCTTCGTGTC-CCCACAGCACG-3' [SEQ ID No. 97] and DRB-R1: 5'-GC- CGCTGCACTGTGAAGCTCTC-3' [SEQ ID No. 98] and a 29 ASO probes (as listed in Table 3-4) were tested of which 18 were found to be best for the identification of the HLA-DRB alleles. In the case of DQB1 genotypes, PCR is carried out using DQB-E2-F2: 5'-CGGTGATTCCCCGCAGAGGAT-3' [SEQ ID No. 99] and DQB-E2-R2: 5'-CCACCTCGTAGT-TGTGTCTGC-3' [SEQ ID No. 100] as primers (see Table 6) which are able to generate a 260 bp. The 24 SSO probes are used as capture probes for this DQB1 classification during hybridization.

To identify DPB1 genotypes, a total of 43 ASO probes were tested of which a set of 35 SSO Probes are shown in Table 7 as the example. In order to amplify a target gene or sequence to a detectable level for hybridization, multiplex PCR amplifications are carried out with a set of primers as shown in Table 8. Primer1-f, Primer2-f and Primer3-f are used for forward priming. Primers4-r, Primer5-r and Primer6-r are used for reversed priming. These primer pairs are able to generate about 264 bp amplicons of 5' end-labeled for hybridization with color development to identify the genotypes in question.

EQUIVALENTS

Those skilled in the art will recognize, or be able to ascertain using no more than routine experimentation, many equivalents to the specific embodiments of the invention described herein. Such equivalents are intended to be encompassed by the following claims.

REFERENCE

1. Bunce M et al. (1995) Tissue Antigens, 46, 355-367.
2. Mach B et al. (1990) in Molecular Biology of HLA Class II Antigens, ed. Silver J (CRC, Boca Raton, Fla.), pp. 201-223.
3. Joseph Wing On Tam, "Flow Through Nucleic Acid Hybridisation Device", U.S. Pat. No. 6,020,187.
4. Thomas E D (1983) J. Clinical Oncology 1, 517-531).
5. Robinson J, Matthew J. Waller, et al., IMGT/HLA and IMGT/MHC: sequence databases for the study of the major histocompatibility complex, Nucleic Acids Res. 2003 January 1;31(1):311-4.
6. Robinson J, Waller M J, Parham P, Bodmer J G, Marsh S G., IMGT/HLA Database—a sequence database for the human major histocompatibility complex, Nucleic Acids Res. 2001 January 1;29(1):210-3.
7. Kaneshige T et. Al., Rapid and Practical HLA Class II Genotyping by Reversed Dot Blotting, Transplantation Proceedings, 1993 February; 25(1): 194-198.
8. Mach et al., "DNA sequences coding for the DR beta-chain locus of the human lymphocyte antigen complex and polypeptides, diagnostic typing processes and products related thereto", U.S. Pat. No. 6,818,393, Nov. 16, 2004.
9. ChowRand Tonai R., "High throughput methods for HLA typing", U.S. Pat. No. 6,670,124, Dec. 30, 2003.
10. Chakraborty R, Stivers D N. Paternity exclusion by DNA markers: effects of paternal mutations. J Forensic Sci 1996 Jul.; 41(4): 671-7.
11. Edwards A, Civitello A, Hammond H A, Caskey C T. DNA typing and genetic mapping with trimeric and tetrameric tandem repeats. Am J Hum Genet. 1991 Oct.; 49(4): 746-56.
12. Gill P, Jeffreys A J, Werrett D J. Forensic application of DNA 'fingerprints'. Nature. 1985 Dec. 12-18;318(6046): 577-9.
13. Weiss K M. In search of human variation. Genome Res 1998 July; 8(7): 691-7
14. Zhao L P, Aragaki C, Hsu L, Quiaoit F. Mapping of complex traits by single-nucleotide polymorphisms. Am J Hum Genet 1998 July; 63(1): 225-40.
15. Brightwell et al. SNP genotyping using a simple and rapid single-tube modification of ARMS illustrated by analysis of 6 SNPs in a population of males with FRAXA repeat expansions. Mol Cell Probes. 2002 August;16(4):297-305.

What is claimed is:

1. A method for rapid identification of HLA Class II genotype of a subject, comprising the steps of:
   (a) obtaining a sample comprising a template nucleic acid from the subject;
   (b) amplifying the template nucleic acid with primers having the sequences of SEQ ID NOs 97-106, thereby generating HLA amplicons; and
   (c) hybridizing the HLA amplicons with immobilized oligonucleotide probes having the sequences of SEQ ID NOs 1, 2, 4, 5, 7, 8, 10, 12-15, 17, 19-21, 24, 26, 29-55, 57-64, 66, 67, 69-88, and 90-92 wherein the resulting hybridization profile would indicate the HLA Class II genotype of the subject.

2. The method of claim 1, wherein the primers having the sequences of SEQ ID Nos. 97-98 are used for identifying HLA-DR genotype.

3. The method of claim 1, wherein the probes having the sequences of SEQ ID Nos. 1, 2, 4, 5, 7, 8, 10, 12-15, 17, 19-21, 24, 26, and 29 are used for identifying HLA-DR genotype.

4. The method of claim 1, wherein the primers having the sequences of SEQ ID Nos. 99-100 are used for identifying HLA-DQ genotype.

5. The method of claim 1, wherein the probes having the sequences of SEQ ID Nos. 30-53 are used for identifying HLA-DQ genotype.

6. The method of claim 1, wherein the primers having the sequences of SEQ ID Nos. 101-106 are used for identifying HLA-DP genotype.

7. The method of claim 1, wherein the probes having the sequences of SEQ ID Nos. 54-55, 57-64, 66, 67, 69-88, and 90-92 are used for identifying HLA-DP genotype.

8. The method of claim 1, wherein the primers comprises a signal generating label.

9. The method of claim 1, wherein the probes are immobilized on a flow-through membrane.

10. The method of claim 9, wherein hybridization of the HLA amplicons with the plurality of immobilized oligonucleotide probes is carried out in a lateral flow-through process wherein sensitivity of hybridization depends on the ratio of the area comprising the probes to the cross section of the membrane.

11. A method of rapid DNA fingerprinting of a subject, comprising the steps of:
   a) obtaining a sample comprising template nucleic acid molecules from the subject;
   b) amplifying the template nucleic acid molecules with primers having the sequences of SEQ ID NOs 97-106, wherein the primers flank one or more loci of interest and comprise signal generating labels;
   c) immobilizing oligonucleotide capture probes on a membrane, wherein the probes have the sequences of SEQ ID NOs 1, 2, 4, 5, 7, 8, 10, 12-15, 17, 19-21, 24, 26, 29-55, 57-64, 66, 67, 69-88, and 90-92;
   d) applying the amplified nucleic acid molecules in a hybridization solution to the membrane without prehybridization; and
   e) hybridizing the amplified nucleic acid molecules with the oligonucleotide capture probes, wherein the hybridization is carried out in a lateral flow-through process wherein sensitivity of the hybridization depends on the ratio of the area comprising the probes to the cross section of the membrane.

12. The method of claim 11, wherein the one or more loci of interest comprise single nucleotide polymorphism loci.

13. The method of claim 11, wherein the one or more loci of interest comprise HLA Class II loci.

14. The method of claim 13, wherein for identifying HLA-DR genotype the primers used are SEQ ID Nos. 97-98, and the probes used are SEQ ID Nos. 1, 2, 4, 5, 7, 8, 10, 12-15, 17, 19-21, 24, 26, and 29.

15. The method of claim 13, wherein for identifying HLA-DQ genotype the primers used are SEQ ID Nos. 99-100, and the probes used are SEQ ID NOs 30-53.

16. The method of claim 13, wherein for identifying HLA-DP genotype the primers used are SEQ ID Nos. 101-106, and the probes used are SEQ ID NOs 54-55, 57-64, 66, 67, 69-88, and 90-92.

* * * * *